(12) United States Patent
Pereira

(10) Patent No.: US 6,514,701 B1
(45) Date of Patent: Feb. 4, 2003

(54) ANTIMICROBIAL PEPTIDES AND METHODS OF USE THEREOF

(75) Inventor: H. Anne Pereira, Edmond, OK (US)

(73) Assignee: The Board of Regents of the University of Oklahoma

( * ) Notice: Subject to any disclaimer, the term of this patent is extended or adjusted under 35 U.S.C. 154(b) by 174 days.

(21) Appl. No.: 09/619,283

(22) Filed: Jul. 19, 2000

Related U.S. Application Data

(62) Division of application No. 09/258,934, filed on Mar. 1, 1999, now Pat. No. 6,107,460.

(51) Int. Cl.[7] ................................................ C12Q 1/68
(52) U.S. Cl. ........................ 435/6; 435/91.1; 435/91.2; 435/212; 514/12; 514/14; 514/15; 514/16; 514/21; 424/85.1; 530/324; 530/326; 530/328; 530/329; 530/335; 530/350; 530/827; 530/829; 530/402

(58) Field of Search ........................... 435/6, 91.1, 91.2, 435/212; 514/12, 14, 15, 16, 21; 424/85.1; 530/324, 326, 328, 329, 335, 350, 827, 829, 402

(56) References Cited

U.S. PATENT DOCUMENTS 5,650,392 A * 7/1997 Pereira et al. ................. 514/12
6,107,460 A * 8/2000 Pereira ......................... 530/326

* cited by examiner

Primary Examiner—Stephanie Zitomer
Assistant Examiner—Janell E. Taylor
(74) Attorney, Agent, or Firm—Dunlap, Codding, & Rogers, P.C.

(57) ABSTRACT

Novel peptide analogs derived from the native sequences of CAP37 peptides 20–44 and 23–42, and their use as therapeutics against bacterial infections and diseases caused by bacterial infection. The peptide analog includes a serine or threonine substitution at one of the two cysteine residues at positions 26 and 42. Substitutions of the native peptide are also contemplated.

1 Claim, 20 Drawing Sheets

Peptide 20-44 and analogs

```
       20                           26                                42
       N-Q-G-R-H-F-C-G-G-A-L-I-H-A-R-F-V-M-T-A-A-S-C-F-Q-                    20-44
       N-Q-G-R-H-F-S-G-G-A-L-I-H-A-R-F-V-M-T-A-A-S-S-F-Q-                    20-44 ser 26/42
       N-Q-G-R-H-F-S-G-G-A-L-I-H-A-R-F-V-M-T-A-A-S-C-F-Q-                    20-44 ser 26
       N-Q-G-R-H-F-C-G-G-A-L-I-H-A-R-F-V-M-T-A-A-S-S-F-Q-                    20-44 ser 42
       N-Q-G-R-H-F-C-G-G-A-L-I-H-A-R-F-V-M-T-A-A-S-C-F-Q-                    20-44 ACM
                   |                                 |
                  ACM                               ACM N-Q-G-R-H-F-C-G-G-A-L-I-H-A-R-F-V-M-T-A-A-H-C-F-Q-                    20-44 his 41
       N-Q-G-R-H-F-C-G-G-A-L-I-H-A-R-F-V-M-T-A-A-R-C-F-Q-                    20-44 arg 41
       N-Q-G-R-H-F-C-G-G-A-L-I-H-A-R-F-V-M-T-A-A-K-C-F-Q-                    20-44 lys 41

N-Q-G-R-H-F-C-A-G-A-L-I-H-A-R-F-V-M-T-A-A-S-C-F-Q-                    20-44 ala 27
       N-Q-G-R-H-F-C-G-A-A-L-I-H-A-R-F-V-M-T-A-A-S-C-F-Q-                    20-44 ala 28
       N-Q-G-R-H-F-C-A-A-A-L-I-H-A-R-F-V-M-T-A-A-S-C-F-Q-                    20-44 ala 27/28

N-Q-G-R-H-F-C-G-G-A-L-I-H-A-R-F-V-M-T-A-A-T-C-F-Q-                    20-44 thr 41

N-Q-G-R-H-F-C-G-G-A-L-I-H-A-R-F-L-M-T-A-A-S-C-F-Q-                    20-44 leu 36
       N-Q-G-R-H-F-C-G-G-A-L-I-H-A-R-F-I-M-T-A-A-S-C-F-Q-                    20-44 ile 36
       N-Q-G-R-H-F-C-G-G-A-L-I-H-A-R-F-A-M-T-A-A-S-C-F-Q-                    20-44 ala 36

N-Q-G-R-H-Y-C-G-G-A-L-I-H-A-R-F-V-M-T-A-A-S-C-F-Q-                    20-44 tyr 25
       N-Q-G-R-H-F-C-G-G-A-L-I-H-A-R-Y-V-M-T-A-A-S-C-F-Q                     20-44 tyr 35
       N-Q-G-R-H-F-C-G-G-A-L-I-H-A-R-F-V-M-T-A-A-S-C-Y-Q                     20-44 tyr 43
```

Fig. 1

SEQUENCE LISTING

```
<160> NUMBER OF SEQ ID NOS: 60

<210> SEQ ID NO 1
<211> LENGTH: 25
<212> TYPE: PRT
<213> ORGANISM: Homo Sapiens

<400> SEQUENCE: 1

Asn Gln Gly Arg His Phe Cys Gly Gly Ala Leu Ile His Ala Arg Phe
1               5                   10                  15

Val Met Thr Ala Ala Ser Cys Phe Gln
            20                  25

<210> SEQ ID NO 2
<211> LENGTH: 20
<212> TYPE: PRT
<213> ORGANISM: Homo Sapiens

<400> SEQUENCE: 2

Arg His Phe Cys Gly Gly Ala Leu Ile His Ala Arg Phe Val Met Thr
1               5                   10                  15

Ala Ala Ser Cys
            20

<210> SEQ ID NO 3
<211> LENGTH: 25
<212> TYPE: PRT
<213> ORGANISM: Homo Sapiens

<400> SEQUENCE: 3
```

-continued

```
Asn Gln Gly Arg His Phe Ser Gly Gly Ala Leu Ile His Ala Arg Phe
1               5                   10                  15

Val Met Thr Ala Ala Ser Cys Phe Gln
            20                  25

<210> SEQ ID NO 4
<211> LENGTH: 20
<212> TYPE: PRT
<213> ORGANISM: Homo Sapiens

<400> SEQUENCE: 4

Arg His Phe Ser Gly Gly Ala Leu Ile His Ala Arg Phe Val Met Thr
1               5                   10                  15

Ala Ala Ser Cys
            20

<210> SEQ ID NO 5
<211> LENGTH: 25
<212> TYPE: PRT
<213> ORGANISM: Homo Sapiens

<400> SEQUENCE: 5

Asn Gln Gly Arg His Phe Cys Gly Gly Ala Leu Ile His Ala Arg Phe
1               5                   10                  15

Val Met Thr Ala Ala Ser Ser Phe Gln
            20                  25

<210> SEQ ID NO 6
<211> LENGTH: 20
<212> TYPE: PRT
<213> ORGANISM: Homo Sapiens

<400> SEQUENCE: 6

Arg His Phe Cys Gly Gly Ala Leu Ile His Ala Arg Phe Val Met Thr
1               5                   10                  15

Ala Ala Ser Ser
            20

<210> SEQ ID NO 7
<211> LENGTH: 25
<212> TYPE: PRT
<213> ORGANISM: Homo Sapiens

<400> SEQUENCE: 7

Asn Gln Gly Arg His Phe Ser Gly Gly Ala Leu Ile His Ala Arg Phe
1               5                   10                  15

Val Met Thr Ala Ala Ser Ser Phe Gln
            20                  25

<210> SEQ ID NO 8
<211> LENGTH: 20
<212> TYPE: PRT
<213> ORGANISM: Homo Sapiens

<400> SEQUENCE: 8

Arg His Phe Ser Gly Gly Ala Leu Ile His Ala Arg Phe Val Met Thr
1               5                   10                  15

Ala Ala Ser Ser
            20

<210> SEQ ID NO 9
<211> LENGTH: 20
```

```
<212> TYPE: PRT
<213> ORGANISM: Homo Sapiens

<400> SEQUENCE: 9

Arg His Phe Ser Gly Gly Ala Leu Ile His Ala Arg Phe Val Met Thr
1               5                   10                  15

Ala Ala Ser Ser
            20

<210> SEQ ID NO 10
<211> LENGTH: 25
<212> TYPE: PRT
<213> ORGANISM: Homo Sapiens

<400> SEQUENCE: 10

Asn Gln Gly Arg His Phe Cys Gly Gly Ala Leu Ile His Ala Arg Phe
1               5                   10                  15

Val Met Thr Ala Ala Arg Cys Phe Gln
            20                  25

<210> SEQ ID NO 11
<211> LENGTH: 25
<212> TYPE: PRT
<213> ORGANISM: Homo Sapiens

<400> SEQUENCE: 11

Asn Gln Gly Arg His Phe Cys Gly Gly Ala Leu Ile His Ala Arg Phe
1               5                   10                  15

Val Met Thr Ala Ala Lys Cys Phe Gln
            20                  25

<210> SEQ ID NO 12
<211> LENGTH: 20
<212> TYPE: PRT
<213> ORGANISM: Homo Sapiens

<400> SEQUENCE: 12

Arg His Phe Cys Gly Gly Ala Leu Ile His Ala Arg Phe Val Met Thr
1               5                   10                  15

Ala Ala His Cys
            20

<210> SEQ ID NO 13
<211> LENGTH: 20
<212> TYPE: PRT
<213> ORGANISM: Homo Sapiens

<400> SEQUENCE: 13

Arg His Phe Cys Gly Gly Ala Leu Ile His Ala Arg Phe Val Met Thr
1               5                   10                  15

Ala Ala Arg Cys
            20

<210> SEQ ID NO 14
<211> LENGTH: 20
<212> TYPE: PRT
<213> ORGANISM: Homo Sapiens

<400> SEQUENCE: 14

Arg His Phe Cys Gly Gly Ala Leu Ile His Ala Arg Phe Val Met Thr
1               5                   10                  15

Ala Ala Lys Cys
```

-continued

```
<210> SEQ ID NO 15
<211> LENGTH: 25
<212> TYPE: PRT
<213> ORGANISM: Homo Sapiens

<400> SEQUENCE: 15

Asn Gln Gly Arg His Phe Ser Gly Gly Ala Leu Ile His Ala Arg Phe
 1               5                  10                  15

Val Met Thr Ala Ala His Cys Phe Gln
            20                  25

<210> SEQ ID NO 16
<211> LENGTH: 25
<212> TYPE: PRT
<213> ORGANISM: Homo Sapiens

<400> SEQUENCE: 16

Asn Gln Gly Arg His Phe Ser Gly Gly Ala Leu Ile His Ala Arg Phe
 1               5                  10                  15

Val Met Thr Ala Ala Arg Cys Phe Gln
            20                  25

<210> SEQ ID NO 17
<211> LENGTH: 25
<212> TYPE: PRT
<213> ORGANISM: Homo Sapiens

<400> SEQUENCE: 17

Asn Gln Gly Arg His Phe Ser Gly Gly Ala Leu Ile His Ala Arg Phe
 1               5                  10                  15

Val Met Thr Ala Ala Lys Cys Phe Gln
            20                  25

<210> SEQ ID NO 18
<211> LENGTH: 25
<212> TYPE: PRT
<213> ORGANISM: Homo Sapiens

<400> SEQUENCE: 18

Asn Gln Gly Arg His Phe Cys Gly Gly Ala Leu Ile His Ala Arg Phe
 1               5                  10                  15

Val Met Thr Ala Ala His Ser Phe Gln
            20                  25

<210> SEQ ID NO 19
<211> LENGTH: 25
<212> TYPE: PRT
<213> ORGANISM: Homo Sapiens

<400> SEQUENCE: 19

Asn Gln Gly Arg His Phe Cys Gly Gly Ala Leu Ile His Ala Arg Phe
 1               5                  10                  15

Val Met Thr Ala Ala Arg Ser Phe Gln
            20                  25

<210> SEQ ID NO 20
<211> LENGTH: 25
<212> TYPE: PRT
<213> ORGANISM: Homo Sapiens

<400> SEQUENCE: 20
```

Asn Gln Gly Arg His Phe Cys Gly Gly Ala Leu Ile His Ala Arg Phe
1               5                   10                  15

Val Met Thr Ala Ala Lys Ser Phe Gln
            20                  25

<210> SEQ ID NO 21
<211> LENGTH: 20
<212> TYPE: PRT
<213> ORGANISM: Homo Sapiens

<400> SEQUENCE: 21

Arg His Phe Ser Gly Gly Ala Leu Ile His Ala Arg Phe Val Met Thr
1               5                   10                  15

Ala Ala His Cys
            20

<210> SEQ ID NO 22
<211> LENGTH: 20
<212> TYPE: PRT
<213> ORGANISM: Homo Sapiens

<400> SEQUENCE: 22

Arg His Phe Ser Gly Gly Ala Leu Ile His Ala Arg Phe Val Met Thr
1               5                   10                  15

Ala Ala Arg Cys
            20

<210> SEQ ID NO 23
<211> LENGTH: 20
<212> TYPE: PRT
<213> ORGANISM: Homo Sapiens

<400> SEQUENCE: 23

Arg His Phe Ser Gly Gly Ala Leu Ile His Ala Arg Phe Val Met Thr
1               5                   10                  15

Ala Ala Lys Cys
            20

<210> SEQ ID NO 24
<211> LENGTH: 20
<212> TYPE: PRT
<213> ORGANISM: Homo Sapiens

<400> SEQUENCE: 24

Arg His Phe Cys Gly Gly Ala Leu Ile His Ala Arg Phe Val Met Thr
1               5                   10                  15

Ala Ala His Ser
            20

<210> SEQ ID NO 25
<211> LENGTH: 20
<212> TYPE: PRT
<213> ORGANISM: Homo Sapiens

<400> SEQUENCE: 25

Arg His Phe Cys Gly Gly Ala Leu Ile His Ala Arg Phe Val Met Thr
1               5                   10                  15

Ala Ala Arg Ser
            20

<210> SEQ ID NO 26

```
<211> LENGTH: 20
<212> TYPE: PRT
<213> ORGANISM: Homo Sapiens

<400> SEQUENCE: 26

Arg His Phe Cys Gly Gly Ala Leu Ile His Ala Arg Phe Val Met Thr
1               5                   10                  15

Ala Ala Lys Ser
            20

<210> SEQ ID NO 27
<211> LENGTH: 25
<212> TYPE: PRT
<213> ORGANISM: Homo Sapiens

<400> SEQUENCE: 27

Asn Gln Gly Arg His Phe Cys Ala Gly Ala Leu Ile His Ala Arg Phe
1               5                   10                  15

Val Met Thr Ala Ala Ser Cys Phe Gln
            20                  25

<210> SEQ ID NO 28
<211> LENGTH: 25
<212> TYPE: PRT
<213> ORGANISM: Homo Sapiens

<400> SEQUENCE: 28

Asn Gln Gly Arg His Phe Cys Gly Ala Ala Leu Ile His Ala Arg Phe
1               5                   10                  15

Val Met Thr Ala Ala Ser Cys Phe Gln
            20                  25

<210> SEQ ID NO 29
<211> LENGTH: 25
<212> TYPE: PRT
<213> ORGANISM: Homo Sapiens

<400> SEQUENCE: 29

Asn Gln Gly Arg His Phe Cys Ala Ala Ala Leu Ile His Ala Arg Phe
1               5                   10                  15

Val Met Thr Ala Ala Ser Cys Phe Gln
            20                  25

<210> SEQ ID NO 30
<211> LENGTH: 25
<212> TYPE: PRT
<213> ORGANISM: Homo Sapiens

<400> SEQUENCE: 30

Asn Gln Gly Arg His Phe Ser Ala Gly Ala Leu Ile His Ala Arg Phe
1               5                   10                  15

Val Met Thr Ala Ala Ser Cys Phe Gln
            20                  25

<210> SEQ ID NO 31
<211> LENGTH: 25
<212> TYPE: PRT
<213> ORGANISM: Homo Sapiens

<400> SEQUENCE: 31

Asn Gln Gly Arg His Phe Ser Gly Ala Ala Leu Ile His Ala Arg Phe
1               5                   10                  15
```

Val Met Thr Ala Ala Ser Cys Phe Gln
            20                  25

<210> SEQ ID NO 32
<211> LENGTH: 25
<212> TYPE: PRT
<213> ORGANISM: Homo Sapiens

<400> SEQUENCE: 32

Asn Gln Gly Arg His Phe Ser Ala Ala Leu Ile His Ala Arg Phe
1               5                   10                  15

Val Met Thr Ala Ala Ser Cys Phe Gln
            20                  25

<210> SEQ ID NO 33
<211> LENGTH: 25
<212> TYPE: PRT
<213> ORGANISM: Homo Sapiens

<400> SEQUENCE: 33

Asn Gln Gly Arg His Phe Cys Ala Gly Ala Leu Ile His Ala Arg Phe
1               5                   10                  15

Val Met Thr Ala Ala Ser Ser Phe Gln
            20                  25

<210> SEQ ID NO 34
<211> LENGTH: 25
<212> TYPE: PRT
<213> ORGANISM: Homo Sapiens

<400> SEQUENCE: 34

Asn Gln Gly Arg His Phe Cys Gly Ala Leu Ile His Ala Arg Phe
1               5                   10                  15

Val Met Thr Ala Ala Ser Ser Phe Gln
            20                  25

<210> SEQ ID NO 35
<211> LENGTH: 25
<212> TYPE: PRT
<213> ORGANISM: Homo Sapiens

<400> SEQUENCE: 35

Asn Gln Gly Arg His Phe Cys Ala Ala Ala Leu Ile His Ala Arg Phe
1               5                   10                  15

Val Met Thr Ala Ala Ser Ser Phe Gln
            20                  25

<210> SEQ ID NO 36
<211> LENGTH: 25
<212> TYPE: PRT
<213> ORGANISM: Homo Sapiens

<400> SEQUENCE: 36

Asn Gln Gly Arg His Phe Cys Gly Gly Ala Leu Ile His Ala Arg Phe
1               5                   10                  15

Val Met Thr Ala Ala Thr Cys Phe Gln
            20                  25

<210> SEQ ID NO 37
<211> LENGTH: 25
<212> TYPE: PRT
<213> ORGANISM: Homo Sapiens

```
<400> SEQUENCE: 37

Asn Gln Gly Arg His Phe Cys Gly Gly Ala Leu Ile His Ala Arg Phe
1               5                   10                  15

Leu Met Thr Ala Ala Ser Cys Phe Gln
            20                  25

<210> SEQ ID NO 38
<211> LENGTH: 25
<212> TYPE: PRT
<213> ORGANISM: Homo Sapiens

<400> SEQUENCE: 38

Asn Gln Gly Arg His Phe Cys Gly Gly Ala Leu Ile His Ala Arg Phe
1               5                   10                  15

Ile Met Thr Ala Ala Ser Cys Phe Gln
            20                  25

<210> SEQ ID NO 39
<211> LENGTH: 25
<212> TYPE: PRT
<213> ORGANISM: Homo Sapiens

<400> SEQUENCE: 39

Asn Gln Gly Arg His Phe Cys Gly Gly Ala Leu Ile His Ala Arg Phe
1               5                   10                  15

Ala Met Thr Ala Ala Ser Cys Phe Gln
            20                  25

<210> SEQ ID NO 40
<211> LENGTH: 25
<212> TYPE: PRT
<213> ORGANISM: Homo Sapiens

<400> SEQUENCE: 40

Asn Gln Gly Arg His Tyr Cys Gly Gly Ala Leu Ile His Ala Arg Phe
1               5                   10                  15

Val Met Thr Ala Ala Ser Cys Phe Gln
            20                  25

<210> SEQ ID NO 41
<211> LENGTH: 25
<212> TYPE: PRT
<213> ORGANISM: Homo Sapiens

<400> SEQUENCE: 41

Asn Gln Gly Arg His Phe Cys Gly Gly Ala Leu Ile His Ala Arg Tyr
1               5                   10                  15

Val Met Thr Ala Ala Ser Cys Phe Gln
            20                  25

<210> SEQ ID NO 42
<211> LENGTH: 25
<212> TYPE: PRT
<213> ORGANISM: Homo Sapiens

<400> SEQUENCE: 42

Asn Gln Gly Arg His Phe Cys Gly Gly Ala Leu Ile His Ala Arg Phe
1               5                   10                  15

Val Met Thr Ala Ala Ser Cys Tyr Gln
            20                  25
```

```
<210> SEQ ID NO 43
<211> LENGTH: 20
<212> TYPE: PRT
<213> ORGANISM: Homo Sapiens

<400> SEQUENCE: 43

Arg His Phe Ser Ala Gly Ala Leu Ile His Ala Arg Phe Val Met Thr
1               5                   10                  15

Ala Ala Ser Cys
            20

<210> SEQ ID NO 44
<211> LENGTH: 20
<212> TYPE: PRT
<213> ORGANISM: Homo Sapiens

<400> SEQUENCE: 44

Arg His Phe Ser Gly Ala Ala Leu Ile His Ala Arg Phe Val Met Thr
1               5                   10                  15

Ala Ala Ser Cys
            20

<210> SEQ ID NO 45
<211> LENGTH: 20
<212> TYPE: PRT
<213> ORGANISM: Homo Sapiens

<400> SEQUENCE: 45

Arg His Phe Ser Ala Ala Ala Leu Ile His Ala Arg Phe Val Met Thr
1               5                   10                  15

Ala Ala Ser Cys
            20

<210> SEQ ID NO 46
<211> LENGTH: 20
<212> TYPE: PRT
<213> ORGANISM: Homo Sapiens

<400> SEQUENCE: 46

Arg His Phe Ser Gly Gly Ala Leu Ile His Ala Arg Phe Leu Met Thr
1               5                   10                  15

Ala Ala Ser Cys
            20

<210> SEQ ID NO 47
<211> LENGTH: 20
<212> TYPE: PRT
<213> ORGANISM: Homo Sapiens

<400> SEQUENCE: 47

Arg His Phe Ser Gly Gly Ala Leu Ile His Ala Arg Phe Ile Met Thr
1               5                   10                  15

Ala Ala Ser Cys
            20

<210> SEQ ID NO 48
<211> LENGTH: 20
<212> TYPE: PRT
<213> ORGANISM: Homo Sapiens

<400> SEQUENCE: 48

Arg His Phe Ser Gly Gly Ala Leu Ile His Ala Arg Phe Ala Met Thr
1               5                   10                  15
```

Ala Ala Ser Cys
        20

<210> SEQ ID NO 49
<211> LENGTH: 20
<212> TYPE: PRT
<213> ORGANISM: Homo Sapiens

<400> SEQUENCE: 49

Arg His Tyr Ser Gly Gly Ala Leu Ile His Ala Arg Phe Val Met Thr
1               5                   10                  15

Ala Ala Ser Cys
        20

<210> SEQ ID NO 50
<211> LENGTH: 20
<212> TYPE: PRT
<213> ORGANISM: Homo Sapiens

<400> SEQUENCE: 50

Arg His Phe Ser Gly Gly Ala Leu Ile His Ala Arg Tyr Val Met Thr
1               5                   10                  15

Ala Ala Ser Cys
        20

<210> SEQ ID NO 51
<211> LENGTH: 20
<212> TYPE: PRT
<213> ORGANISM: Homo Sapiens

<400> SEQUENCE: 51

Arg His Phe Cys Ala Gly Ala Leu Ile His Ala Arg Phe Val Met Thr
1               5                   10                  15

Ala Ala Ser Ser
        20

<210> SEQ ID NO 52
<211> LENGTH: 20
<212> TYPE: PRT
<213> ORGANISM: Homo Sapiens

<400> SEQUENCE: 52

Arg His Phe Cys Gly Ala Ala Leu Ile His Ala Arg Phe Val Met Thr
1               5                   10                  15

Ala Ala Ser Ser
        20

<210> SEQ ID NO 53
<211> LENGTH: 20
<212> TYPE: PRT
<213> ORGANISM: Homo Sapiens

<400> SEQUENCE: 53

Arg His Phe Cys Ala Ala Ala Leu Ile His Ala Arg Phe Val Met Thr
1               5                   10                  15

Ala Ala Ser Ser
        20

<210> SEQ ID NO 54
<211> LENGTH: 20
<212> TYPE: PRT
<213> ORGANISM: Homo Sapiens

<400> SEQUENCE: 54

Arg His Phe Cys Gly Gly Ala Leu Ile His Ala Arg Phe Leu Met Thr
1               5                   10                  15

Ala Ala Ser Ser
            20

<210> SEQ ID NO 55
<211> LENGTH: 20
<212> TYPE: PRT
<213> ORGANISM: Homo Sapiens

<400> SEQUENCE: 55

Arg His Phe Cys Gly Gly Ala Leu Ile His Ala Arg Phe Ile Met Thr
1               5                   10                  15

Ala Ala Ser Ser
            20

<210> SEQ ID NO 56
<211> LENGTH: 20
<212> TYPE: PRT
<213> ORGANISM: Homo Sapiens

<400> SEQUENCE: 56

Arg His Phe Cys Gly Gly Ala Leu Ile His Ala Arg Phe Ala Met Thr
1               5                   10                  15

Ala Ala Ser Ser
            20

<210> SEQ ID NO 57
<211> LENGTH: 20
<212> TYPE: PRT
<213> ORGANISM: Homo Sapiens

<400> SEQUENCE: 57

Arg His Tyr Cys Gly Gly Ala Leu Ile His Ala Arg Phe Val Met Thr
1               5                   10                  15

Ala Ala Ser Ser
            20

<210> SEQ ID NO 58
<211> LENGTH: 20
<212> TYPE: PRT
<213> ORGANISM: Homo Sapiens

<400> SEQUENCE: 58

Arg His Phe Cys Gly Gly Ala Leu Ile His Ala Arg Tyr Val Met Thr
1               5                   10                  15

Ala Ala Ser Ser
            20

<210> SEQ ID NO 59
<211> LENGTH: 20
<212> TYPE: PRT
<213> ORGANISM: Artificial sequence
<220> FEATURE:
<223> OTHER INFORMATION: Completely synthesized
<221> NAME/KEY: MISC_FEATURE
<222> LOCATION: (3)..(3)
<223> OTHER INFORMATION: phe or tyr
<221> NAME/KEY: MISC_FEATURE
<222> LOCATION: (5)..(5)
<223> OTHER INFORMATION: gly or ala
<221> NAME/KEY: MISC_FEATURE

```
<222> LOCATION: (6)..(6)
<223> OTHER INFORMATION: gly or ala
<221> NAME/KEY: MISC_FEATURE
<222> LOCATION: (7)..(7)
<223> OTHER INFORMATION: ala, leu, ile or val
<221> NAME/KEY: MISC_FEATURE
<222> LOCATION: (8)..(8)
<223> OTHER INFORMATION: ala, leu, ile or val
<221> NAME/KEY: MISC_FEATURE
<222> LOCATION: (9)..(9)
<223> OTHER INFORMATION: ala, leu, ile or val
<221> NAME/KEY: MISC_FEATURE
<222> LOCATION: (11)..(11)
<223> OTHER INFORMATION: ala, leu, ile or val
<221> NAME/KEY: MISC_FEATURE
<222> LOCATION: (13)..(13)
<223> OTHER INFORMATION: phe or tyr
<221> NAME/KEY: MISC_FEATURE
<222> LOCATION: (14)..(14)
<223> OTHER INFORMATION: ala, leu, ile or val
<221> NAME/KEY: MISC_FEATURE
<222> LOCATION: (16)..(16)
<223> OTHER INFORMATION: ser or thr
<221> NAME/KEY: MISC_FEATURE
<222> LOCATION: (17)..(17)
<223> OTHER INFORMATION: ala, leu, ile or val
<221> NAME/KEY: MISC_FEATURE
<222> LOCATION: (18)..(18)
<223> OTHER INFORMATION: ala, leu, ile or val
<221> NAME/KEY: MISC_FEATURE
<222> LOCATION: (19)..(19)
<223> OTHER INFORMATION: ser, thr, his, arg or lys
<221> NAME/KEY: MISC_FEATURE
<222> LOCATION: (20)..(20)
<223> OTHER INFORMATION: ser or thr

<400> SEQUENCE: 59

Arg His Xaa Cys Xaa Xaa Xaa Xaa Xaa His Xaa Arg Xaa Xaa Met Xaa
1               5                   10                  15

Xaa Xaa Xaa Xaa
            20

<210> SEQ ID NO 60
<211> LENGTH: 20
<212> TYPE: PRT
<213> ORGANISM: Artificial sequence
<220> FEATURE:
<223> OTHER INFORMATION: Completely synthesized
<221> NAME/KEY: MISC_FEATURE
<222> LOCATION: (3)..(3)
<223> OTHER INFORMATION: phe or tyr
<221> NAME/KEY: MISC_FEATURE
<222> LOCATION: (4)..(4)
<223> OTHER INFORMATION: ser or thr
<221> NAME/KEY: MISC_FEATURE
<222> LOCATION: (5)..(5)
<223> OTHER INFORMATION: gly or ala
<221> NAME/KEY: MISC_FEATURE
<222> LOCATION: (6)..(6)
<223> OTHER INFORMATION: gly or ala
<221> NAME/KEY: MISC_FEATURE
<222> LOCATION: (7)..(7)
<223> OTHER INFORMATION: ala, leu, ile or val
<221> NAME/KEY: MISC_FEATURE
<222> LOCATION: (8)..(8)
<223> OTHER INFORMATION: ala, leu, ile or val
<221> NAME/KEY: MISC_FEATURE
<222> LOCATION: (9)..(9)
<223> OTHER INFORMATION: ala, leu, ile or val
<221> NAME/KEY: MISC_FEATURE
<222> LOCATION: (11)..(11)
<223> OTHER INFORMATION: ala, leu, ile or val
<221> NAME/KEY: MISC_FEATURE
<222> LOCATION: (13)..(13)
<223> OTHER INFORMATION: phe or tyr
<221> NAME/KEY: MISC_FEATURE
```

```
<222> LOCATION: (14)..(14)
<223> OTHER INFORMATION: ala, leu, ile or val
<221> NAME/KEY: MISC_FEATURE
<222> LOCATION: (16)..(16)
<223> OTHER INFORMATION: ser or thr
<221> NAME/KEY: MISC_FEATURE
<222> LOCATION: (17)..(17)
<223> OTHER INFORMATION: ala, leu, ile or val
<221> NAME/KEY: MISC_FEATURE
<222> LOCATION: (18)..(18)
<223> OTHER INFORMATION: ala, leu, ile or val
<221> NAME/KEY: MISC_FEATURE
<222> LOCATION: (19)..(19)
<223> OTHER INFORMATION: ser, thr his, arg or lys

<400> SEQUENCE: 60

Arg His Xaa Xaa Xaa Xaa Xaa Xaa Xaa His Xaa Arg Xaa Xaa Met Xaa
1               5                   10                  15

Xaa Xaa Xaa Cys
            20
```

ANTIMICROBIAL PEPTIDES AND METHODS OF USE THEREOF

CROSS REFERENCE TO RELATED APPLICATIONS

This is a divisional of U.S. Ser. No. 09/258,934, filed Mar. 1, 1999 now U.S. Pat. No. 6,107,460.

STATEMENT REGARDING FEDERALLY SPONSORED RESEARCH OR DEVELOPMENT

Some aspect of this invention were made in the course of Grant RO1 AI 28018 awarded by NIH, and therefore the government may have certain rights in some aspects of this invention.

BACKGROUND

The present invention is related to antimicrobial peptides and methods of use thereof in vivo, and more particularly to substituted derivatives of peptide 20–44 of CAP37.

Antimicrobial therapies have advanced greatly over the years; however, people still die from infections and sepsis. The recent re-emergence of old infections once thought to be on the decline and the rapid evolution of resistant bacterial strains reinforces the critical need for designing and/or discovering new and more effective therapies. The most significant development in it antibiotic therapy in the last decade has been the exploitation of a group of naturally occurring host proteins that are potent antimicrobials, to produce more effective, safer and broader acting drugs.

The immune system has at its disposal a number of mechanisms whereby it may protect itself from invading pathogens. The bactericidal killing mechanisms of the human neutrophil are particularly effective and comprise a collection of cationic granule proteins with potent antimicrobial action. One of these host-defense peptides is a novel, neutrophil protein known as CAP37 (Cationic Antimicrobial Protein of Molecular weight 37 kDa). The first isolation and purification of CAP37 was performed by Spitznagel and colleagues in 1984, who established that CAP37 had very strong antimicrobial activity mainly against gram-negative bacteria (1). Recently we demonstrated that in addition to the previously demonstrated antibiotic activity, CAP37 is a potent and highly specific chemoattractant for monocytes (2). We have determined the complete amino acid sequence of CAP37 (3) and cloned the gene for CAP37 (4). More recently we showed that CAP37 binds endotoxin (5).

Endotoxin is the outer membrane lipopolysaccharide (LPS) component of gram-negative bacteria. Bacterial LPS has very important clinical relevance because of its pleiotropic effect on various immune cells. It can evoke various disease symptoms ranging from chills and fever to circulatory collapse, multiorgan failure and death; a syndrome often referred to as endotoxic or septic shock. Despite aggressive treatment the mortality rates remain high, with septic shock being the most common cause of death in the intensive care unit and the thirteenth leading cause of death overall. Figures from the Centers for Disease Control in Atlanta, Ga. suggest that septic shock occurs at the rate of 175 per 100,000 people with the rate reaching almost 500 per 100,000 hospitalized patients. The death rate is often as high as 25 to 40%. Septic/endotoxic shock has been shown to be most often due to gram-negative bacteria although recent evidence would tend to indicate that the incidence of shock due to gram-positive bacteria and fungi is on the rise. Factors that have contributed to the increasing incidence of sepsis include the new immunosuppressive therapies, invasive devices such as intravenous catheters and surgical devices and an aging population with many chronic diseases that predispose to sepsis.

The component responsible for the toxic effect of the LPS molecule is the lipid component called lipid A. This region is embedded in the outer membrane of the bacterium and believed to be reasonably constant between different species of gram-negative bacteria. The manner in which LPS evokes its lethal effects is by binding to cells such as monocytes, macrophages and/or endothelial cells, triggering them to produce toxic oxygen radicals, cytokines such as tumor necrosis factor α (TNFα), various interleukins (IL-1, IL-6, and IL-8) and numerous other products. Our studies on CAP37 have led to the identification of a 25 amino acid peptide that mimics the antimicrobial and lipopolysaccharide binding functions of the native molecule (6). This synthetic peptide 20–44 based on residues 20 through 44 of native CAP37 has the amino acid sequence NQGRHFCG-GALIHARFVMTAASCFQ (SEQ ID NO:1). This peptide has been tested in vitro and in vivo for antimicrobial activity as well as endotoxin binding activity (6). Peptide 20–44 shows strong in vitro bactericidal activity mainly against gram-negative bacteria such as *Salmonella typhimurium*, *Escherichia coli* and *Pseudomonas aeruginosa*. In addition, the peptide is active against the gram-positive organisms *Enterococcus faecalis* and *Staphylococcus aureus*. In vivo experiments were conducted with peptide 20–44 in a conscious rat model of sepsis using purified endotoxin (5). Intravenous infusion of peptide 20–44 (3.0 mg/kg body weight) with *Escherichia coli* LPS (250 μg/kg over 30 min) into conscious unrestrained rats prevented LPS-induced hyperdynamic and hypodynamic circulatory shock. Peptide 20–44 (0.2, 1.0, and 5.0 mg/kg) administered intravenously to conscious actinomycin-D sensitized rats following a lethal dose of LPS neutralized LPS toxicity, resulting in dose-dependent 7-day survival rates of 30, 50 and 80% respectively. Peptide 20–44 (5.0 mg/kg) significantly inhibited the endotoxin-induced increase in circulating TNFα in sensitized rats. These data demonstrate that peptide 20–44 has the capacity to abolish in vivo biological responses to LPS that are relevant to human sepsis and to significantly neutralize the toxicity of circulating *Escherichia coli* LPS.

The results described above, as well as further information regarding CAP37 peptides and their function are shown in U.S. Pat. Nos. 5,484,885; 5,458,874; 5,607,916; 5,627,262; and 5,650,392, and pending U.S. Ser. No. 08/840,519, the specifications of all of which are hereby incorporated herein by reference in their entireties.

| Table of Abbreviations - Amino Acids | | |
|---|---|---|
| Name | Abbreviations* | |
| Glycine | Gly | G |
| Alanine | Ala | A |
| Valine | Val | V |
| Leucine | Leu | L |
| Isoleucine | Ile | I |
| Methionine | Met | M |
| Phenylalanine | Phe | F |
| Proline | Pro | P |
| Serine | Ser | S |
| Threonine | Thr | T |
| Cysteine | Cys | C |
| Asparagine | Asn | N |
| Glutamine | Gln | Q |

-continued

Table of Abbreviations - Amino Acids

| Name | Abbreviations* | |
|---|---|---|
| Tyrosine | Tyr | Y |
| Tryptophan | Trp | W |
| Aspartic acid | Asp | D |
| Glutamic acid | Glu | E |
| Histidine | His | H |
| Lysine | Lys | K |
| Arginine | Arg | R |

*Where such abbreviations for amino acids are used without an indication of enantiomeric structure, either the L- or D-enantiomers or a mixture of the L- or D-enantiomers may suitably be utilized.

BRIEF DESCRIPTION OF THE INVENTION

The present application describes new peptide analogs (e.g., see FIG. 1) based on the native sequence of CAP37 peptide 20–44 or 23–42 and their use as effective therapeutics against certain bacterial infections and diseases caused by bacterial infection.

In a particularly preferred embodiment, the present invention contemplates a peptide, and a composition comprising said peptide, which is a derivative of CAP37 peptide 23–42 (SEQ ID NO:2) wherein one of the cysteine residues at positions 26 and 42 is substituted with a serine or threonine residue and one of the cysteine residues at positions 26 and 42 is left unsubstituted. Further, the peptide derivative may comprise at least one of the following substitutions: phenylalanine replaced by tyrosine; glycine replaced by alanine; valine replaced by alanine, leucine, or isoleucine; alanine replaced by leucine, isoleucine or valine; leucine replaced by alanine, isoleucine or valine; isoleucine replaced by valine, leucine or alanine; serine replaced by histidine, arginine, or lysine; and threonine replaced by serine.

As noted elsewhere herein, the peptide derivative may be a derivative of CAP 37 peptide 20–44 modified as described above for the derivative of CAP37 peptide 23–42 above.

The invention further comprises a method of treating a bacterial infection or septic shock in a patient, or prophylactically preventing septic shock in a subject comprising administering a therapeutically effective amount of a peptide derivative claimed and described herein.

Further, the peptide derivative contemplated herein may comprise a peptide (SEQ ID NO: 59 and SEQ ID NO: 60) having the formula:

R-H-$X_1$-$X_2$-$X_3$-$X_4$-$X_5$-$X_6$-$X_7$-H-$X_8$-R-$X_9$-$X_{10}$-M-$X_{11}$-$X_{12}$-$X_{13}$-$X_{14}$-$X_{15}$ wherein $X_1$ and $X_9$ are phenylalanine and/or tyrosine; $X_2$ and $X_{15}$ are cysteine, serine, and/or threonine; $X_3$ and $X_4$ are glycine and/or alanine; $X_5$–$X_8$, $X_{10}$, $X_{12}$ and $X_{13}$ are alanine, leucine, isoleucine and/or valine; $X_{11}$ is serine and/or threonine; $X_{14}$ is serine, threonine, histidine, arginine or lysine; R is arginine; H is histidine; M is methionine; and with the proviso that one of $X_2$ and $X_{15}$ is cysteine and one of $X_2$ and $X_{15}$ is serine or threonine.

The present invention further comprises a DNA molecule having a nucleotide sequence encoding a peptide having an amino acid sequence as defined in any of the amino acid sequences listed or described herein, in particular, those having substituted cysteine residues at positions 26 or 42.

BRIEF DESCRIPTION OF THE DRAWINGS

FIG. 1 is a listing of the amino acid sequences of CAP37 peptide 20–44 and analogs thereof.

DETAILED DESCRIPTION OF THE INVENTION

Figure 2:
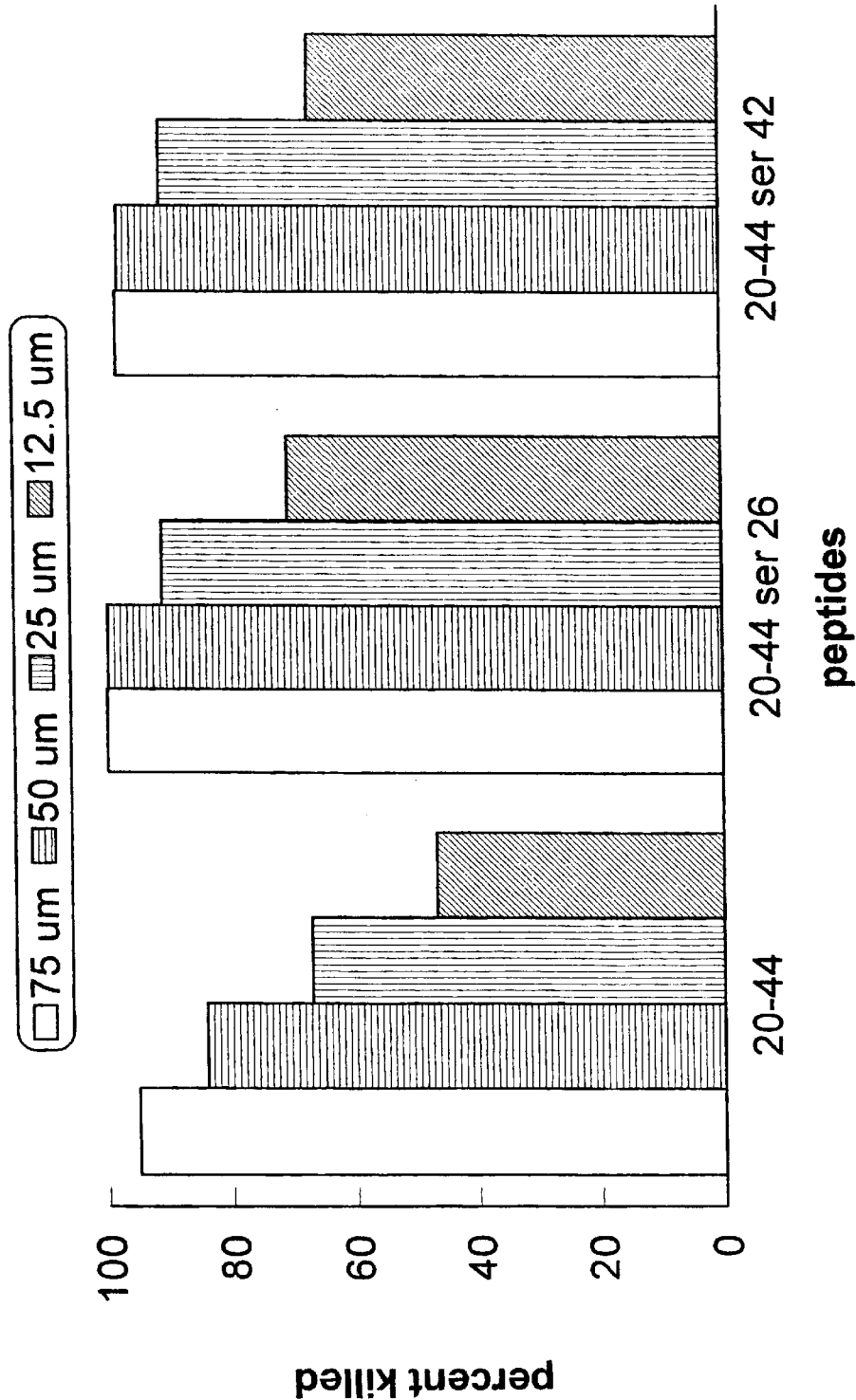
FIG. 2 is a graph showing the bactericidal effects of peptides 20–44, 20–44$_{ser26}$ and 20–44$_{ser42}$ at varying concentrations on *Salmonella typhimurium* SH9178.

The present application describes new peptide analogs (e.g., see FIG. 1) based on the native sequence of CAP37 peptide 20–44 or 23–42 and their use as effective therapeutics against certain bacterial infections and diseases caused by bacterial infection.

In a particularly preferred embodiment, the present invention contemplates a peptide, and a composition comprising said peptide, which is a derivative of CAP37 peptide 23–42 (SEQ ID NO:2) wherein one of the cysteine residues at positions 26 and 42 is substituted with a serine or threonine residue and one of the cysteine residues at positions 26 and 42 is left unsubstituted. Further, the peptide derivative may comprise at least one of the following substitutions: phenylalanine replaced by tyrosine; glycine replaced by alanine; valine replaced by alanine, leucine, or isoleucine; alanine replaced by leucine, isoleucine or valine; leucine replaced by alanine, isoleucine or valine; isoleucine replaced by valine, leucine or alanine; serine replaced by histidine, arginine, or lysine; and threonine replaced by serine.

As noted elsewhere herein, the peptide derivative may be a derivative of CAP37 peptide 20–44 modified as described above for the derivative of CAP37 peptide 23–42 above.

The invention further comprises a method of treating a bacterial infection or septic shock in a patient, or prophylactically preventing septic shock in a subject comprising administering a therapeutically effective amount of a peptide derivative claimed and described herein.

Further, the peptide derivative contemplated herein may comprise a peptide (SEQ ID NO: 59 and SEQ ID NO: 60) having the formula:

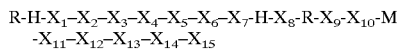

R-H-$X_1$-$X_2$-$X_3$-$X_4$-$X_5$-$X_6$-$X_7$-H-$X_8$-R-$X_9$-$X_{10}$-M-$X_{11}$-$X_{12}$-$X_{13}$-$X_{14}$-$X_{15}$ wherein $X_1$ and $X_9$ are phenylalanine and/or tyrosine; $X_2$ and $X_{15}$ are cysteine, serine, and/or threonine; $X_3$ and $X_4$ are glycine and/or alanine; $X_5$–$X_8$, $X_{10}$, $X_{12}$ and $X_{13}$ are alanine, leucine, isoleucine and/or valine; $X^{11}$ is serine and/or threonine; $X_{14}$ is serine, threonine, histidine, arginine or lysine; R is arginine; H is histidine; M is methionine; and with the proviso that one of $X_2$ and $X_{15}$ is cysteine and one of $X_2$ and $X_{15}$ is serine or threonine.

The present invention further comprises a DNA molecule having a nucleotide sequence encoding a peptide having an amino acid sequence as defined in any of the amino acid sequences listed or described herein, in particular, those having substituted cysteine residues at positions 26 or 42.

Peptide 20–44 of CAP37 in the native form contains two cysteine (cys) residues at positions 26 and 42 which together form a disulfide bridge (3). In order to assess the importance of these two cysteine residues for activity of the peptide, four analogs of the peptide were synthesized and tested for their antibiotic action. Analogs 20–44$_{ser26}$ (SEQ ID NO:3), 20–44$_{ser26}$ (SEQ ID NO:5), and 20–44$_{ser26/42}$ (SEQ ID NO:7) are homologous to the parent peptide, differing only in that serines were substituted for cysteines at positions 26, 42, and 26 and 42, respectively. In the fourth peptide, 20–44$_{ACM}$, the sequence is the same as 20–44 (SEQ ID NO:1) except both cysteines were permanently protected with an ACM (boc-cys-acetamidomethyl) side group and therefore could not readily oxidize to disulfides (6).

Results described herein demonstrate that the novel peptides 20–44$_{ser\ 26}$ and 20–44$_{ser\ 42}$ are effective in inhibiting growth of certain gram-negative and gram-positive bacteria and in blocking release of TNFα from LPS-stimulated macrophages. Methods used herein are those previously described in U.S. Pats. No. 5,607,916; 5,627,262; and 5,650,392.

The finding that derivatives of peptide 20–44 having a substitution of only a single cysteine residue are antimicrobial is a surprising result. Previous work indicated that both cysteines were necessary for activity. For example, U.S. Pat. No. 5,458,874 showed that a derivative of peptide 20–44 having ACM side chains attached to each of the cysteine residues at positions 26 and 42 (i.e., a peptide wherein disulfide bridge formation was prevented), antimicrobial activity was substantially reduced (column 34, lines 41–52). When both cysteine residues at positions 26 and 42 were replaced with serines, antimicrobial activity was eliminated (U.S. Pat. No. 5,607,916, column 5, lines 6–10). It was thus previously believed that the two cysteines at positions 26 and 42 were necessary because of the requirement of a disulfide bridge, and formation of a peptide having a cyclic component (patent '916, column 6, lines 4–6).

These results would suggest that replacement of a single cysteine residue would eliminate or significantly reduce antibacterial activity, contrary to what is taught, described, and enabled herein.

Antibiotic Peptides—in vitro Activity

Figure 3:
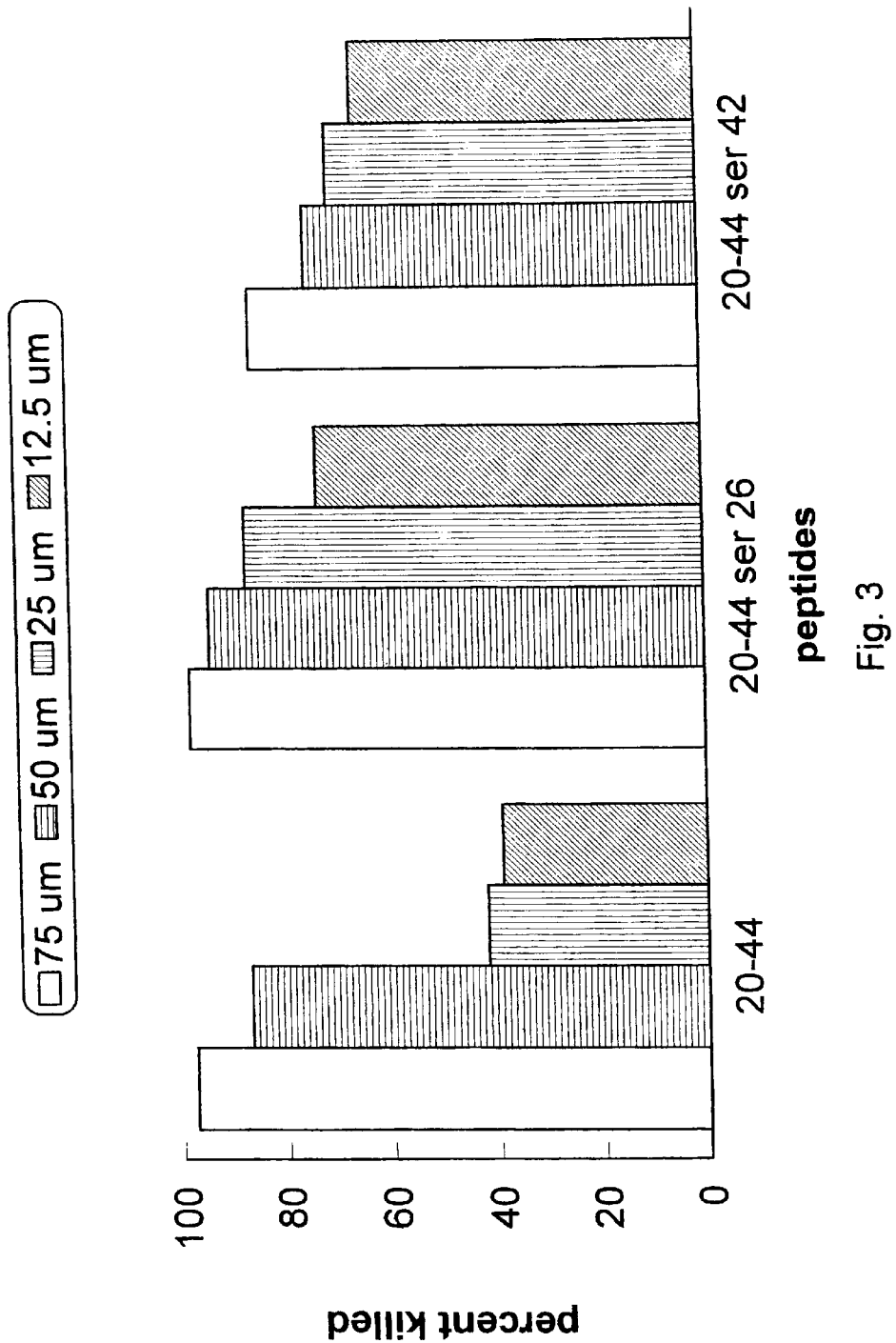
FIG. 3 is a graph showing the bactericidal effects of peptides 20–44, 20–44$_{ser26}$ and 20–44$_{ser42}$ at varying concentrations on *Salmonella typhimurium* LT2.
Figure 4:
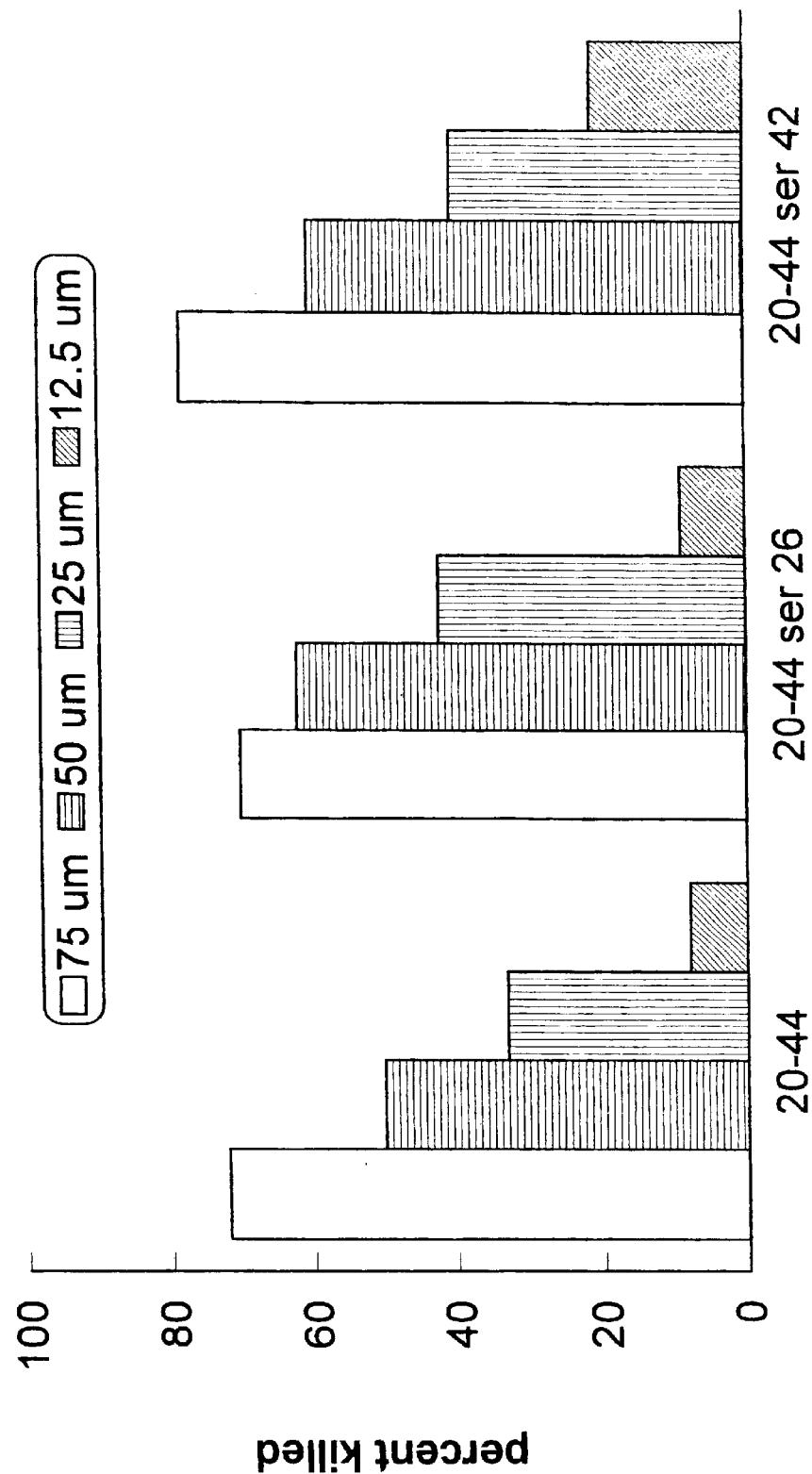
FIG. 4 is a graph showing the bactericidal effects of peptides 20–44, 20–44$_{ser26}$ and 20–44$_{ser42}$ at varying concentrations on *Staphylococcus aureus* ATCC strain 25923.
Figure 5:
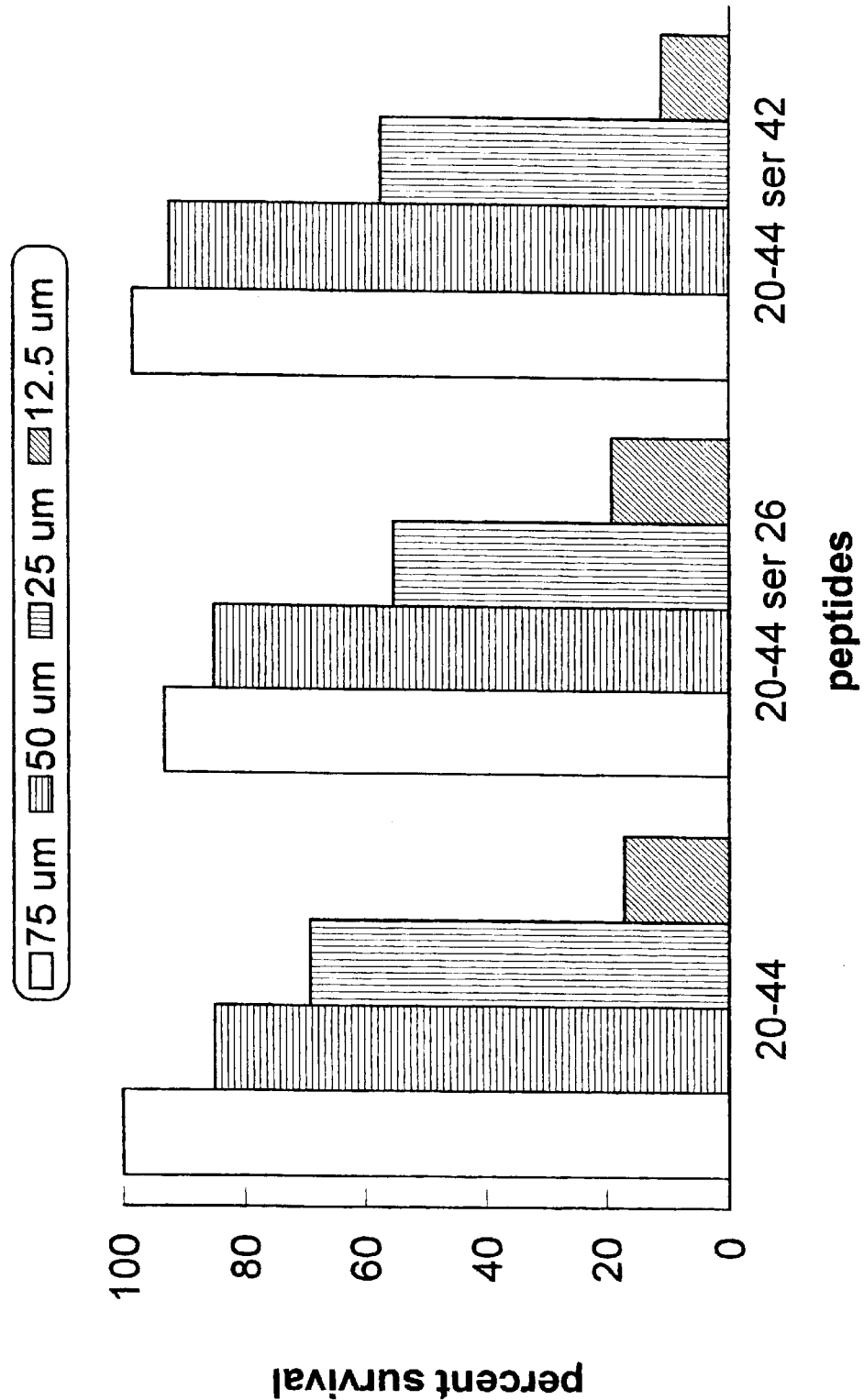
FIG. 5 is a graph showing the bactericidal effects of peptides 20–44, 20–44$_{ser26}$ and 20–44$_{ser42}$ at varying concentrations on *Enterococcus faecalis*.

Peptides 20–44, 20–44$_{ser26}$ and 20–44$_{ser42}$, were assayed for bactericidal activity using *S. typhimurium* SH9178 as the test organism. As shown in FIG. 2, peptide 20–44 had significant antibiotic activity. About 95% of the bacteria were killed at the highest concentration of peptide 20–44 tested (75 μM or 200 μg/ml), and 84% mortality was achieved at 100 μg/ml of the peptide 20–44. Peptides 20–44$_{ser26/42}$ and 20–44$_{ACM}$ have been shown to be ineffective antibiotics (see column 5, lines 6–10 in U.S. Pat. No. 5,607,916 and column 34, lines 45–55 in U.S. Pat. No. 5,458,874). As described herein, peptides in which only one cys residue was replaced by serine (i.e. peptide 20–44$_{ser42}$ and peptide 20–44$_{ser26}$) were as active as the parent peptide. Peptide 20–44$_{ser42}$ killed 97.8% of bacteria at 75 μM, and peptide 20–44$_{ser26}$ killed 99.6% of bacteria at 75 μM. Importantly, at concentrations of only 12.5 μM, peptide 20–44$_{ser26}$ killed 70.4% of organisms and peptide 20–44$_{ser42}$ killed 66.6% of bacteria. We tested these peptides with the smooth, more virulent LT2 strain of *S. typhimurium*, (FIG. 3). Both mono-substituted serine analogs showed strong antibacterial activity against this organism as well. Indeed, the two serine analogs, 20–44$_{ser26}$ and 20–44$_{ser42}$ were able to kill 73% and 65% of bacteria at 12.5 μM, the lowest concentration of peptide tested. These levels of mortality were very much greater than those obtained using peptide 20–44. Two other organisms, *Staphylococcus aureus* ATCC strain 25923 and *Enterococcus faecalis* (a clinical isolate), both of which are gram-positive organisms, were also tested against 20–44$_{ser26}$ and 20–44$_{ser42}$. As indicated in FIGS. 4 and 5, both mono-substituted serine analogs showed potent activity against these two bacterial strains.

LPS Binding Peptides—in vitro Sctivity

Figure 6:
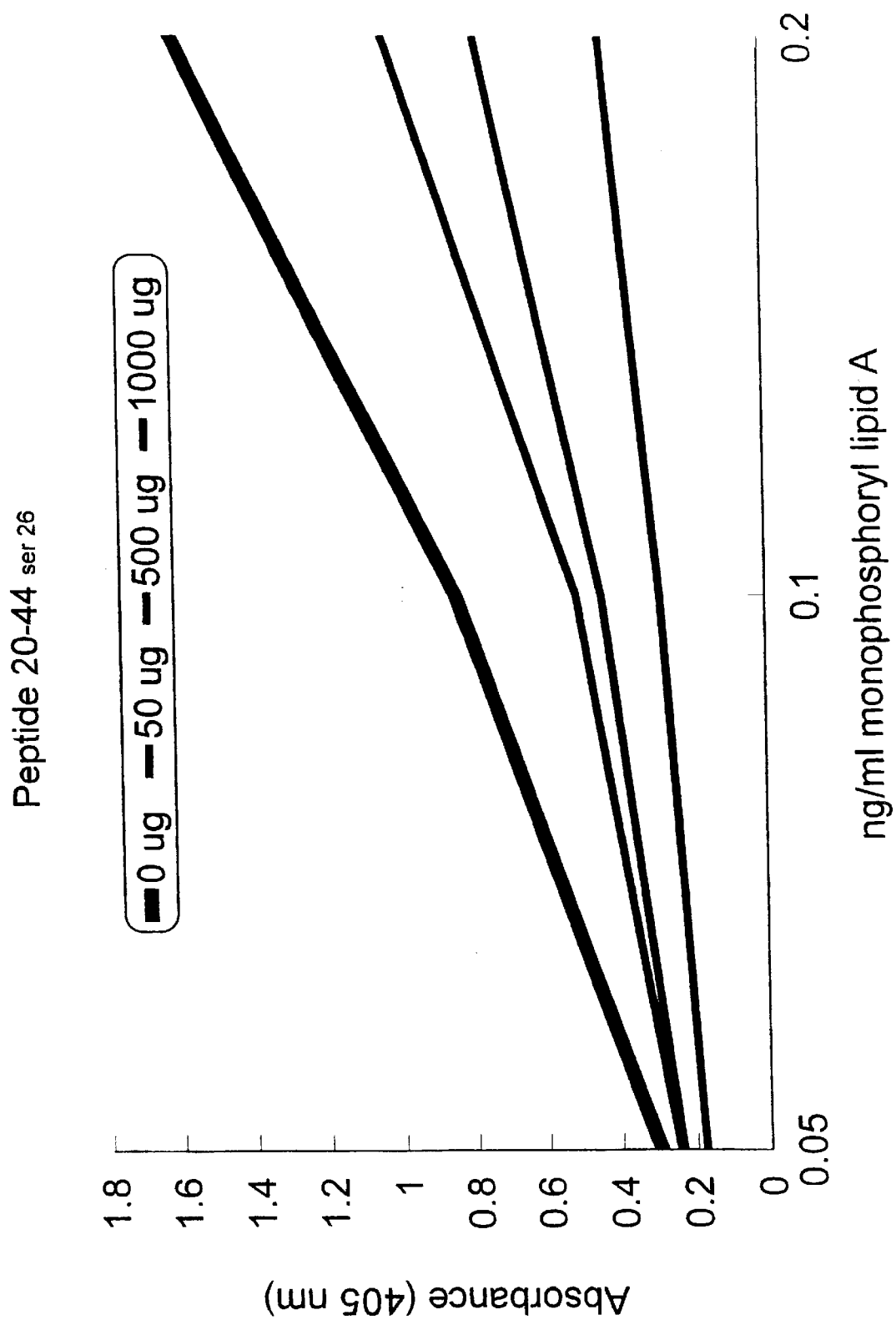
FIG. 6 is a graph showing the binding of peptides 20–44$_{ser26}$ to Lipid A of LPS.

We have previously found that CAP37 binds lipopolysaccharide (LPS) (5, 6) and that the LPS binding and antibacterial domain of CAP37 are coincident (6). We tested the ability of the peptide analogs of the present invention to bind LPS in the in vitro limulus amebocyte lysate (LAL) assay and compared them with the parent peptide, 20–44. Analog 20–44$_{ser26}$ was capable of binding monophosphoryl lipid A, the toxic component of the LPS molecule (FIG. 6).

Figure 7:
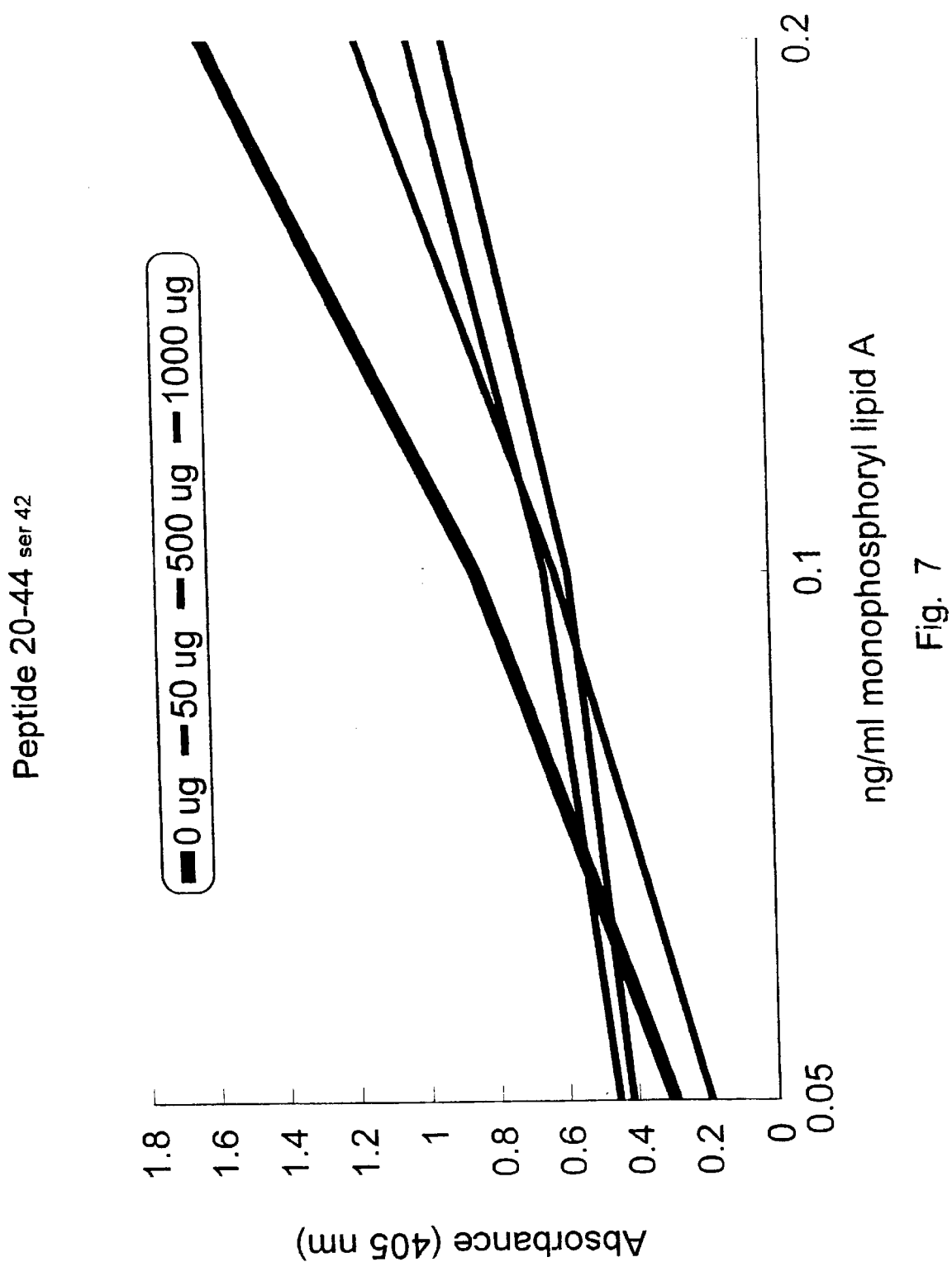
FIG. 7 is a graph showing the binding of peptide 20–44$_{ser42}$ to Lipid A of LPS.
Figure 8:
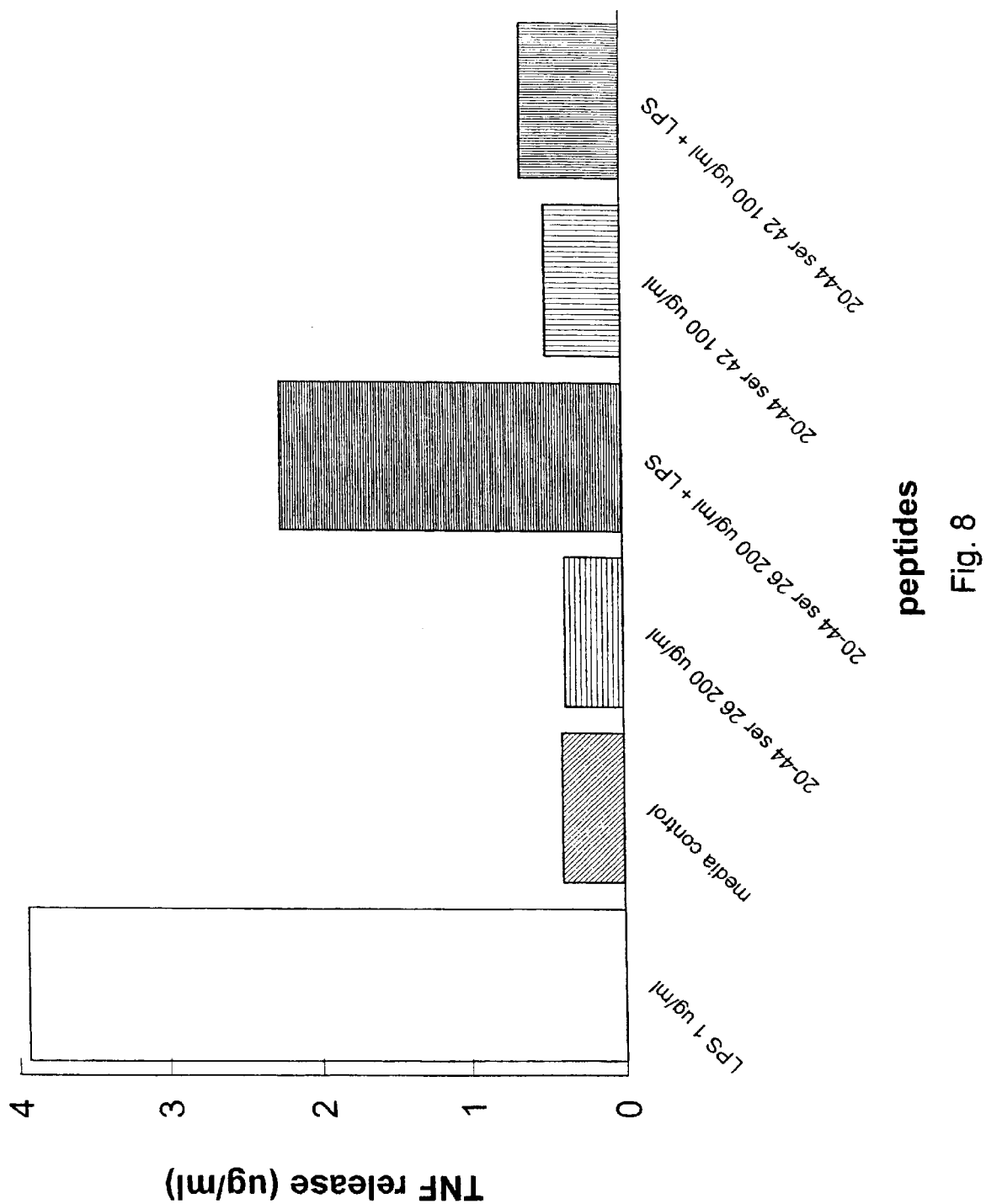
FIG. 8 is a graph showing the effects of various peptides on LPS-mediated release of TNFα in rat macrophages.

Similarly, peptide 20–44$_{ser42}$ was also capable of neutralizing the effect of monophosphoryl lipid A at concentrations greater than 500 μg/ml (FIG. 7) The effects of 20–44$_{ser26}$ at 500 μg/ml and at 1000 μg/ml were particularly potent, since it was able to reduce levels of free endotoxin (LPS) down to baseline levels.

Effect of Peptides on LPS-mediated Release of TNFα

The effects of the serine-substituted peptides on LPS-mediated release of tumor necrosis factor α (TNFα) from rat peritoneal macrophages was explored. The deleterious effects of LPS in sepsis are due to its interaction with macrophages to produce a number of proinflammatory cytokines such as TNFα, interleukin-1 (IL-1), interleukin-6 (IL-6), and interleukin- 8 (IL-8). Since peptide 20–44 and the two serine-substituted analogs 20–44$_{ser26}$ and 20–44$_{ser42}$ bound LPS, we questioned whether the peptides could bind LPS and neutralize the effect of LPS on macrophage release of cytokines. As indicated FIG. 8, 20–44$_{ser42}$ at 100 μg/ml was very effective at blocking TNFα release from LPS stimulated macrophages. Levels of TNF-α were decreased by 83.8%. Peptide 20–44$_{SER26}$ was also capable of neutralizing the effects of LPS, as indicated by the reduction in TNFα levels by 42.9%. These are very significant findings since sometimes when septic patients are treated with conventional antibiotics, they often become more ill. This is because LPS is shed from the bacterium as it is killed, and the conventional antibiotic cannot neutralize the effects of the free LPS. The fact that 20–44$_{ser26}$ and 20–44$_{ser42}$ can actually both kill bacteria, and bind and neutralize LPS, make them very desirable therapeutics for treating infections.

Antibiotic Peptides—in vivo Activity

Figure 9:
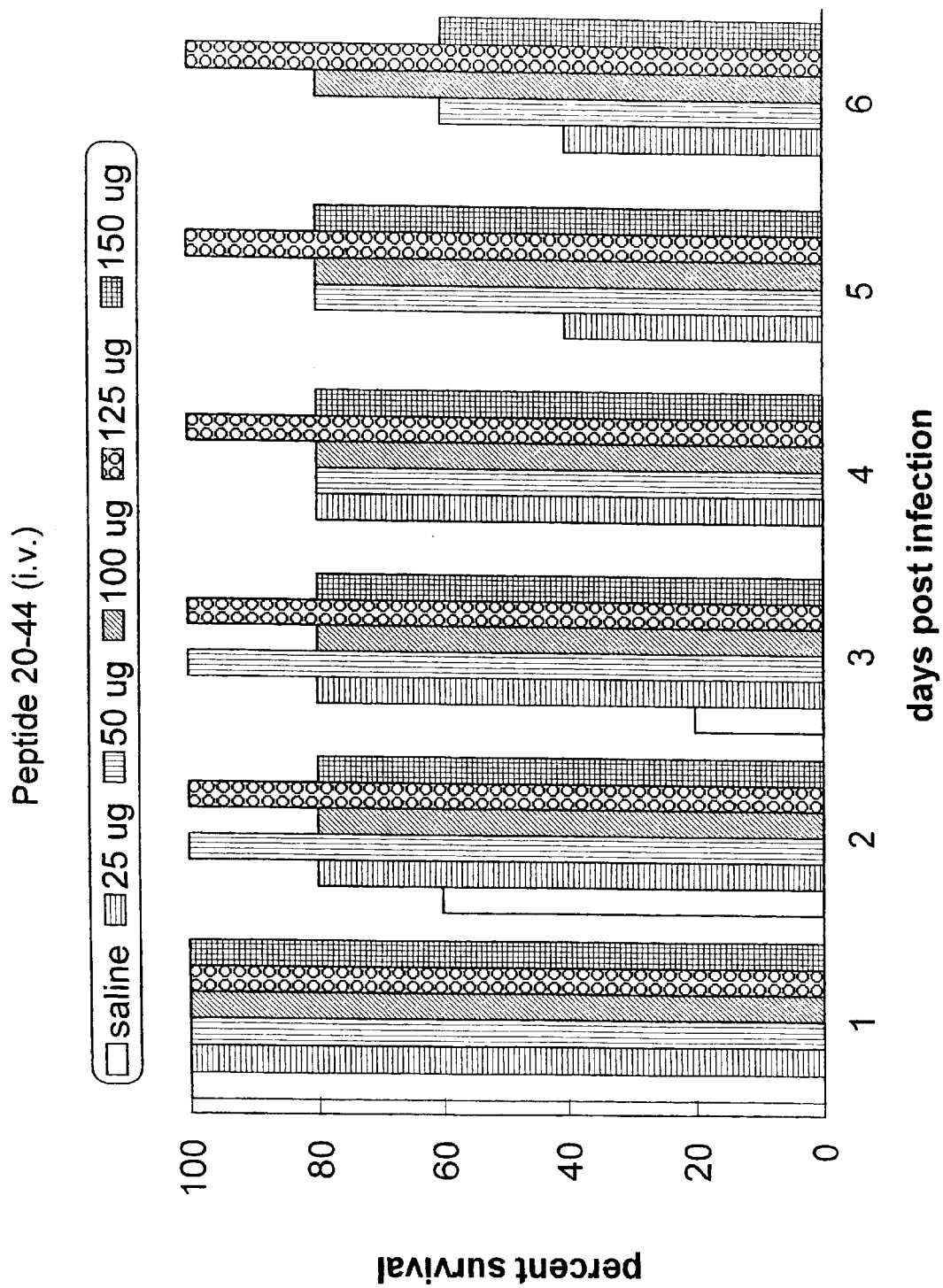
FIG. 9 is a graph showing the effects of various concentrations of peptide 20–44 administered intravenously on survival of mice inoculated with live *Salmonella typhimurium* LT2.
Figure 10:
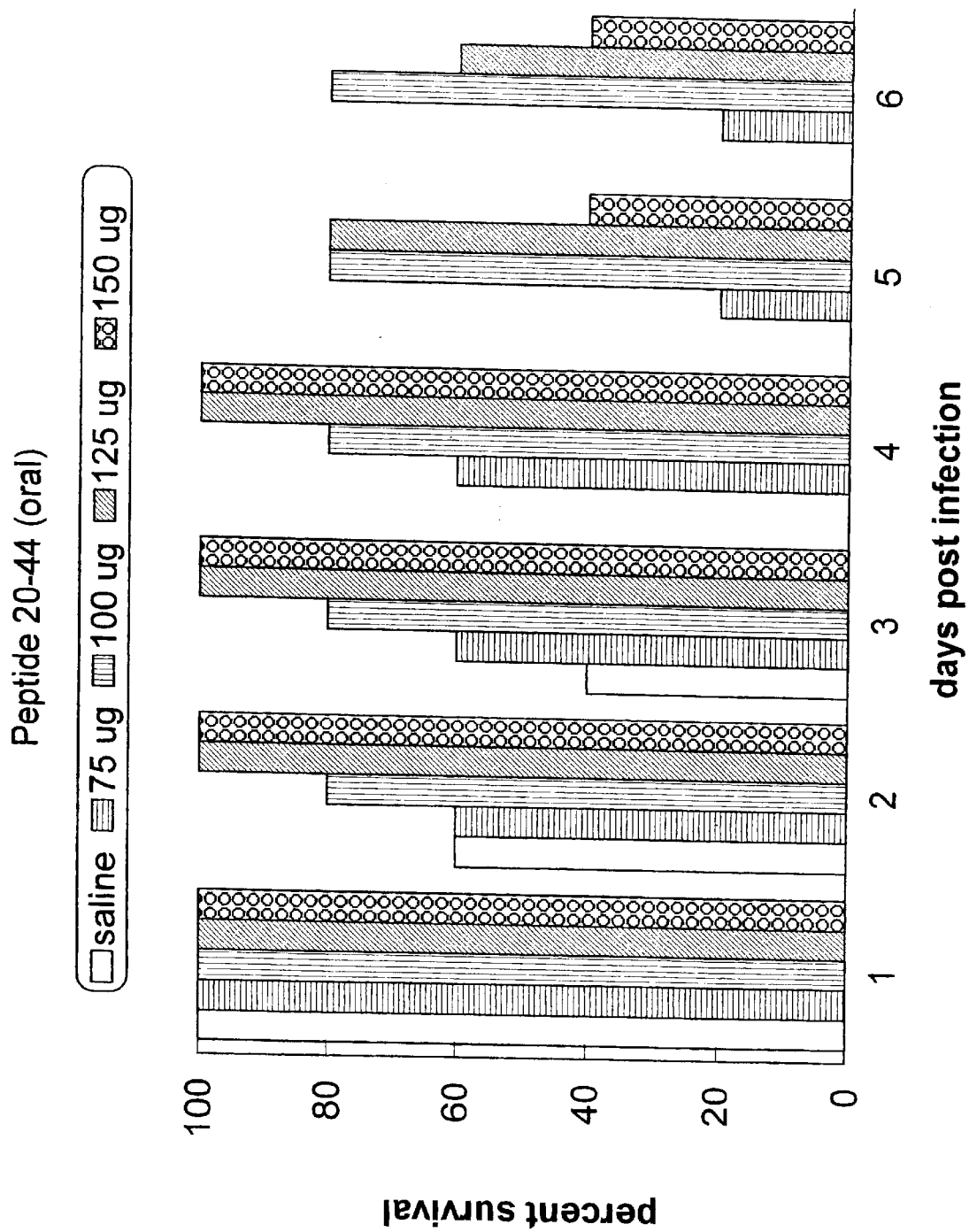
FIG. 10 is a graph showing the effects of various concentrations of peptide 20–44 administered orally on survival of mice inoculated with live *Salmonella typhimurium* LT2.
Figure 11:
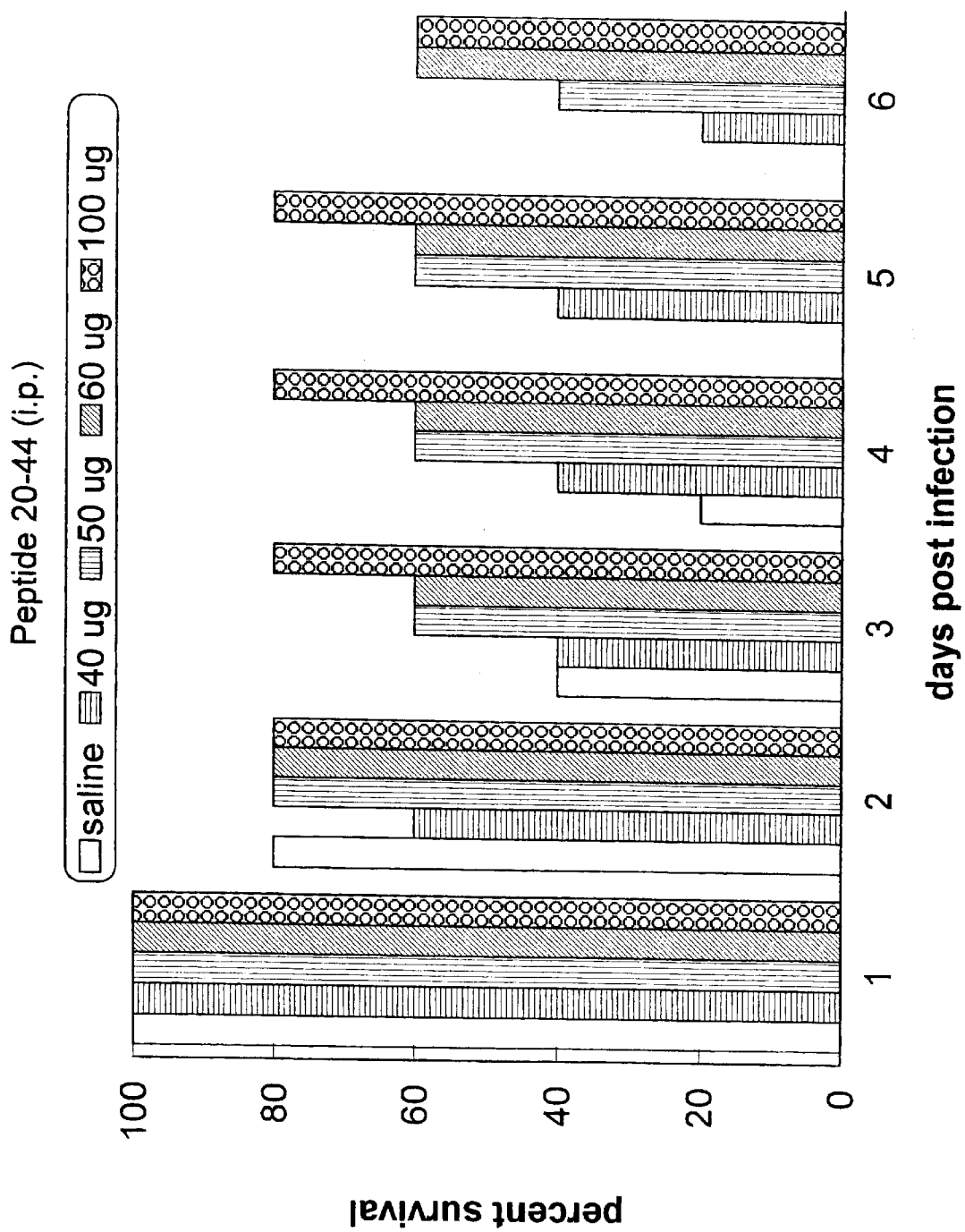
FIG. 11 is a graph showing the effects of various concentrations of peptide 20–44 administered intraperitoneally on survival of mice inoculated with live *Salmonella typhimurium* LT2.
Figure 12:
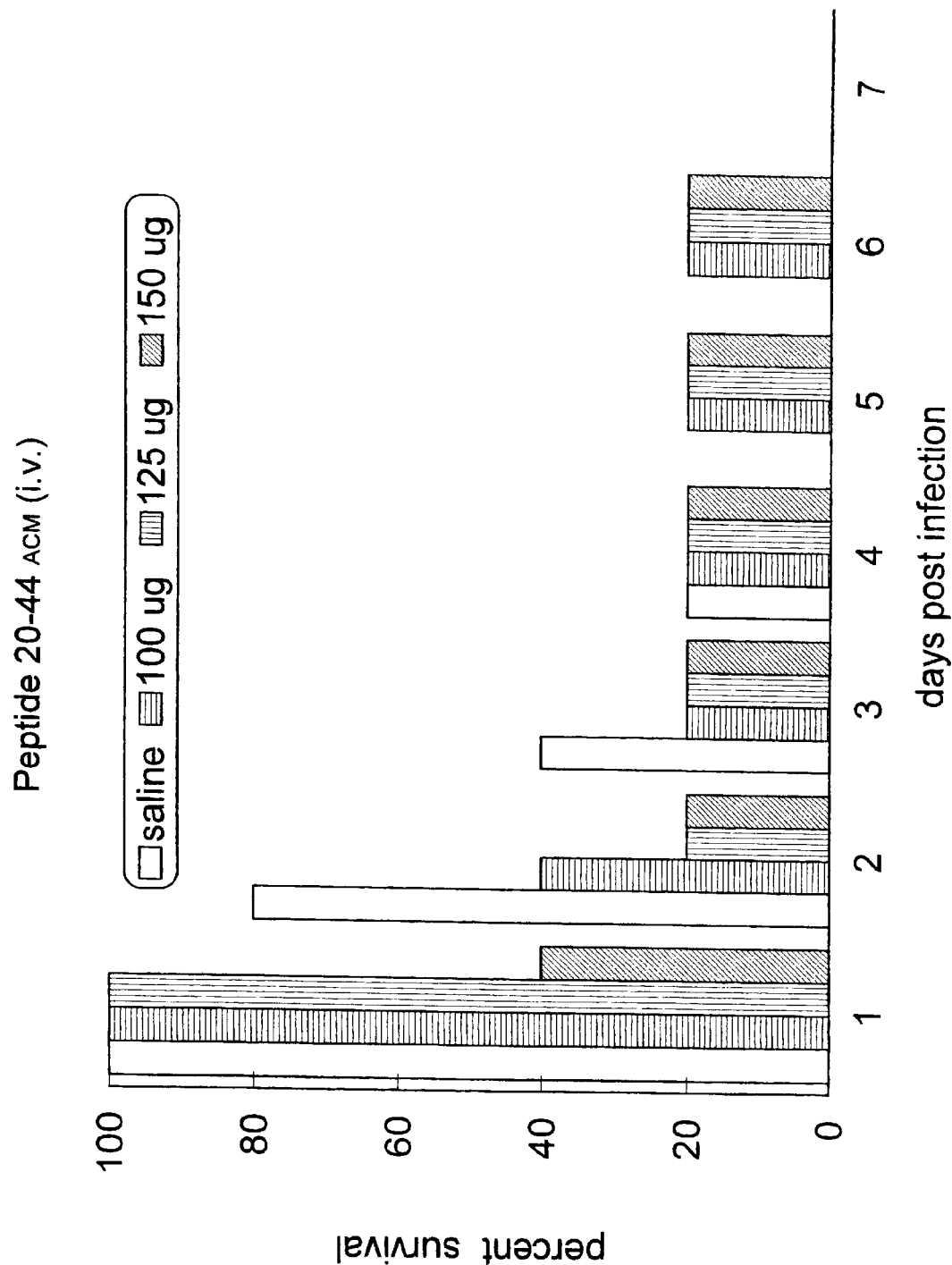
FIG. 12 is a graph showing the effects of various concentrations of peptide 20–44$_{ACM}$ administered intravenously on survival of mice inoculated with live *Salmonella typhimurium* LT2.
Figure 13:
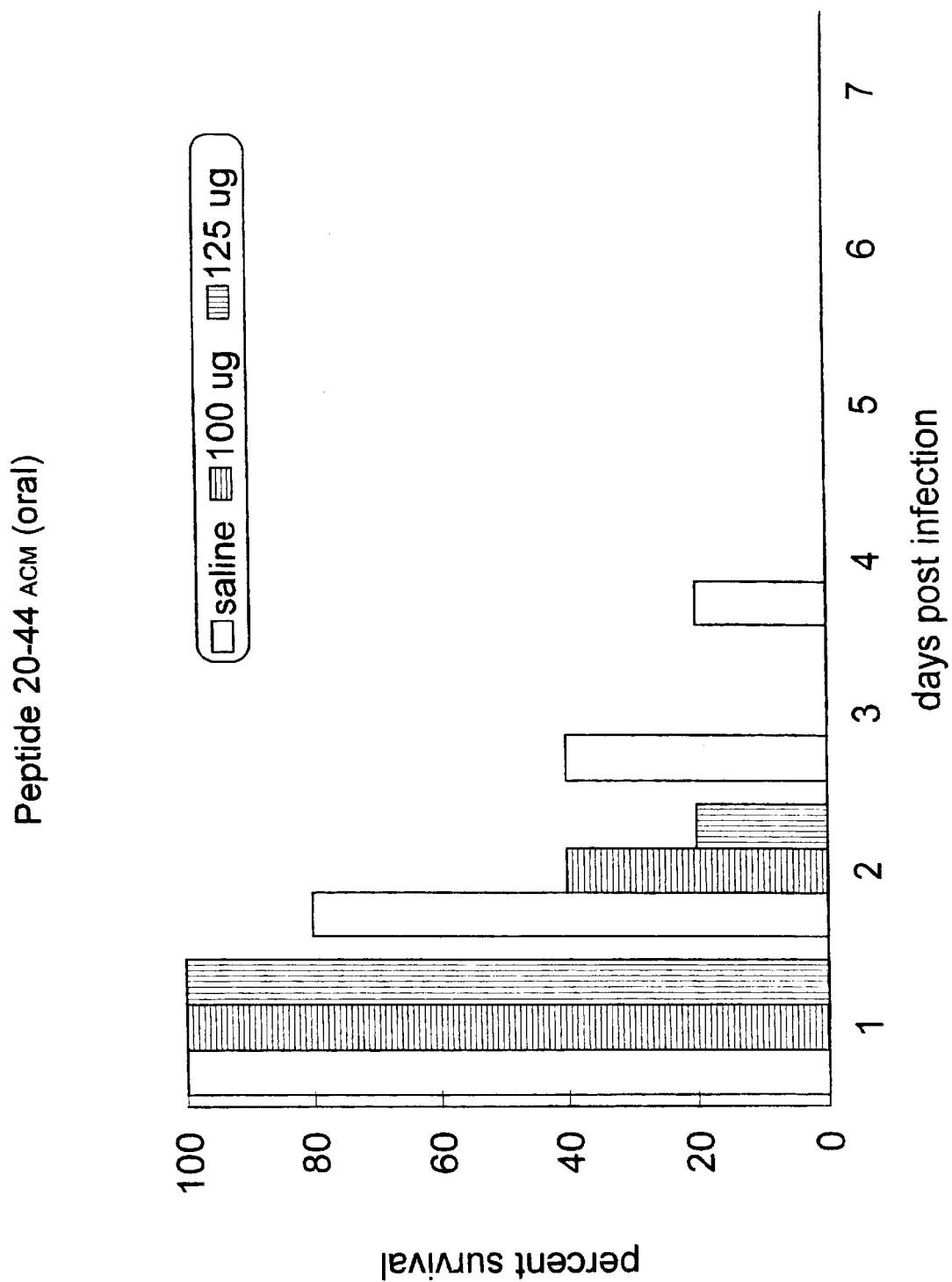
FIG. 13 is a graph showing the effects of various concentrations of peptide 20–44$_{ACM}$ administered orally on survival of mice inoculated with live *Salmonella typhimurium* LT2.
Figure 14:
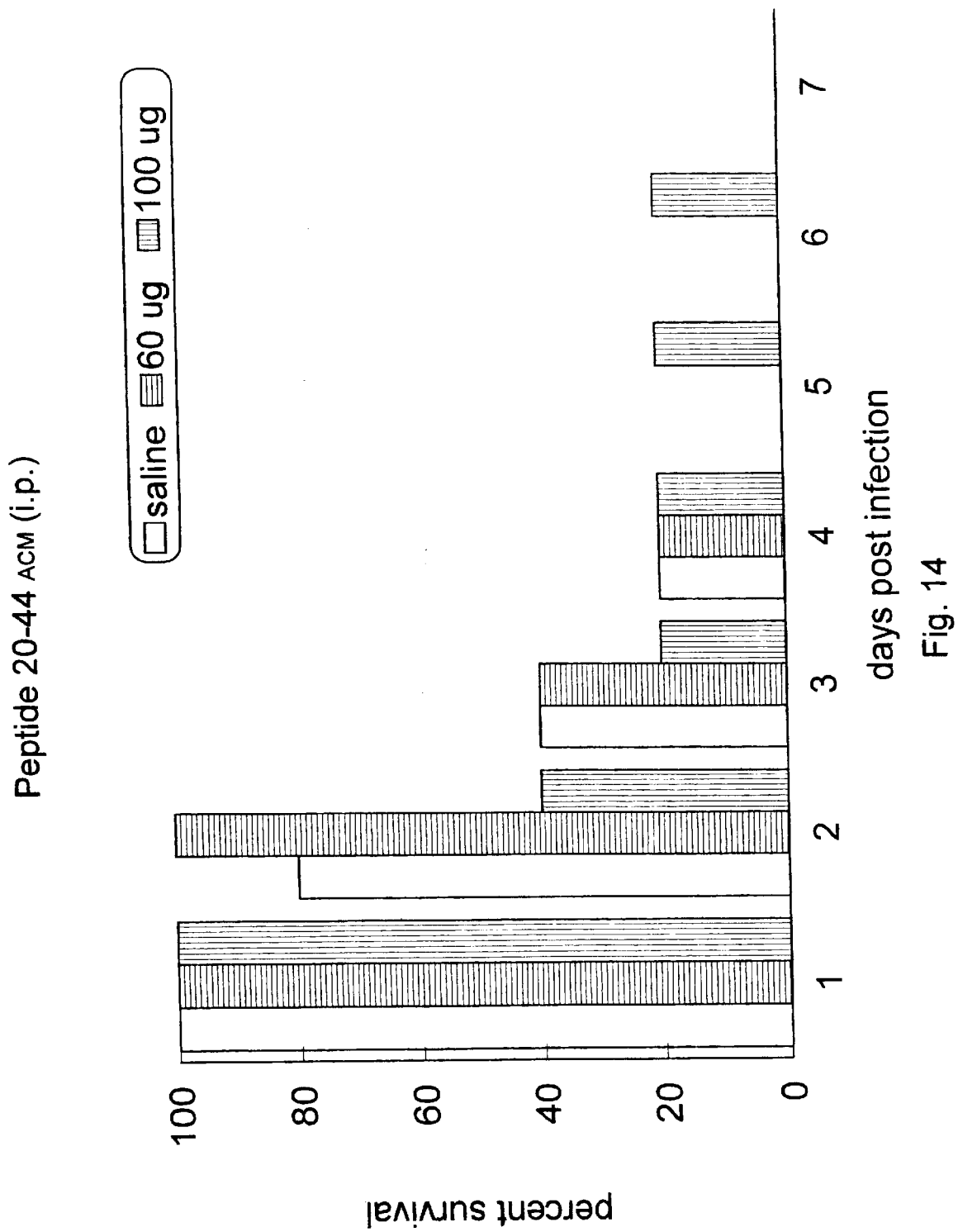
FIG. 14 is a graph showing the effects of various concentrations of peptide 20–44$_{ACM}$ administered intraperitoneally on survival of mice inoculated with live *Salmonella typhimurium* LT2.

Mice (female, Balb/c, 6–8 weeks) were administered a dose of live *S. typhimurium* LT2 (8×10$^8$/mouse) via the oral route. Without treatment, this dose of live organisms led to the death of all animals between day 3 and 4 (i.e. LD$_{100}$ at day 3 or 4). Following challenge with Salmonella, peptide 20–44 (0–150 μg/mouse) was administered via the intravenous, oral, and intraperitoneal routes. The results indicate that peptide 20–44 when administered via the intravenous (FIG. 9), oral (FIG. 10), and intraperitoneal routes (FIG. 11), can rescue animals from lethal infection due to *S. typhimurium*. At day 6 post infection, 100% of animals given a dose of 125 μg of peptide 20–44 intravenously survived. 80% of mice given 50, 100 and 150 μg of peptide survived through to day 5. Data shown in FIG. 10 strongly indicate that peptide 20–44 may also be given via the oral route since 80% survival rates were obtained with 100 μg of peptide. This is evidence that the peptide is not destroyed by the acid environment and enzymes of the stomach and indicates an alternative route of administration to the intravenous route discussed in FIG. 9. The third route of administration of peptide 20–44 was the intraperitoneal route. This is often the method of choice in a veterinary situation. Importantly, the data in FIG. 11 show that the peptide at a dose of 100 μg yields survival rates of 80% and 60% at days 5 and 6 post infection, respectively. Mice treated with the control peptide, 20–44$_{ACM}$, and vehicle/saline alone, succumbed to infection very rapidly after the inoculation with the bacteria (FIGS. 12–14).

Figure 15:
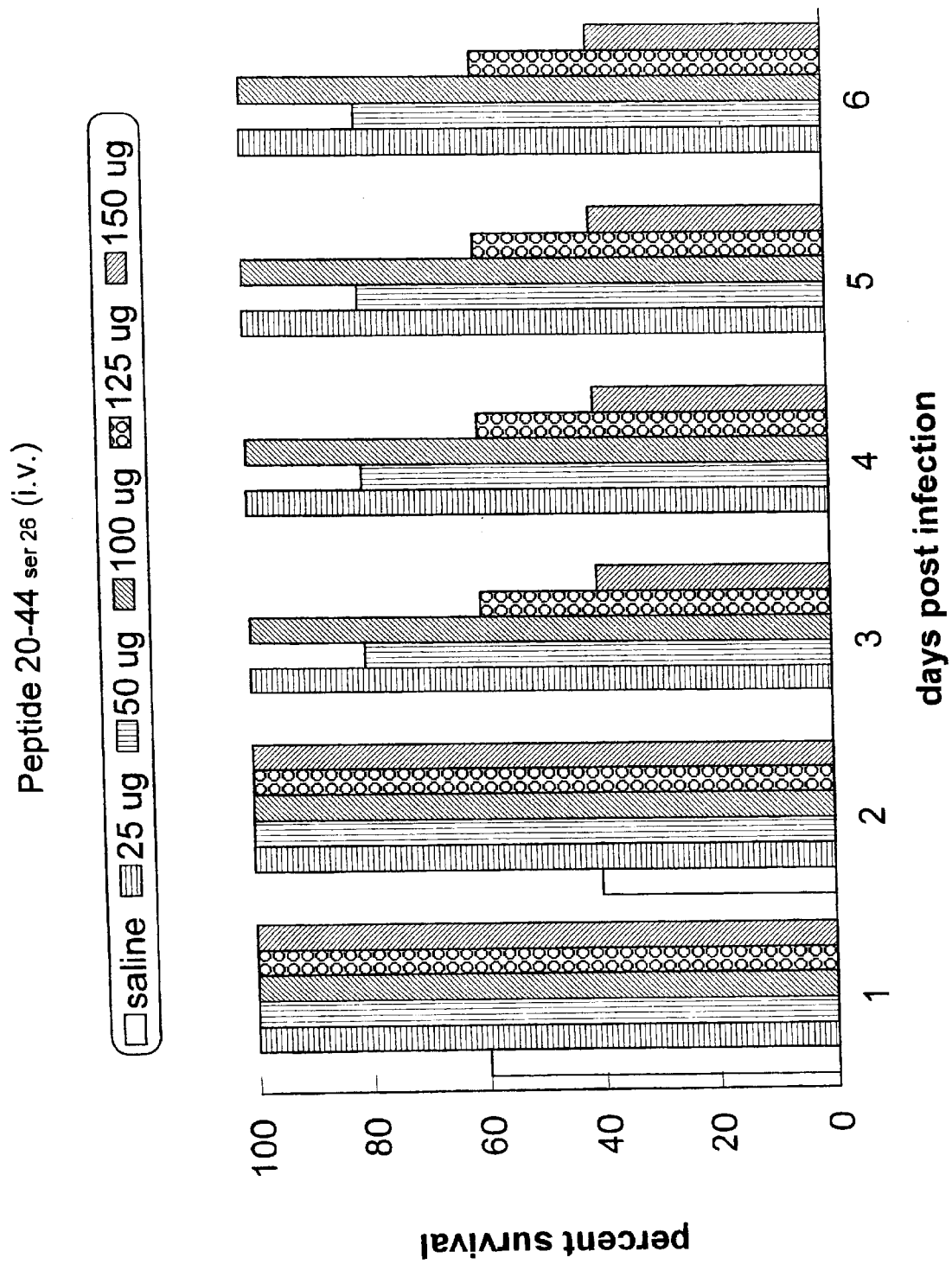
FIG. 15 is a graph showing the effects of various concentrations of peptide 20–44$_{ser26}$ administered intravenously on survival of mice inoculated with live *Salmonella typhimurium* LT2.
Figure 16:
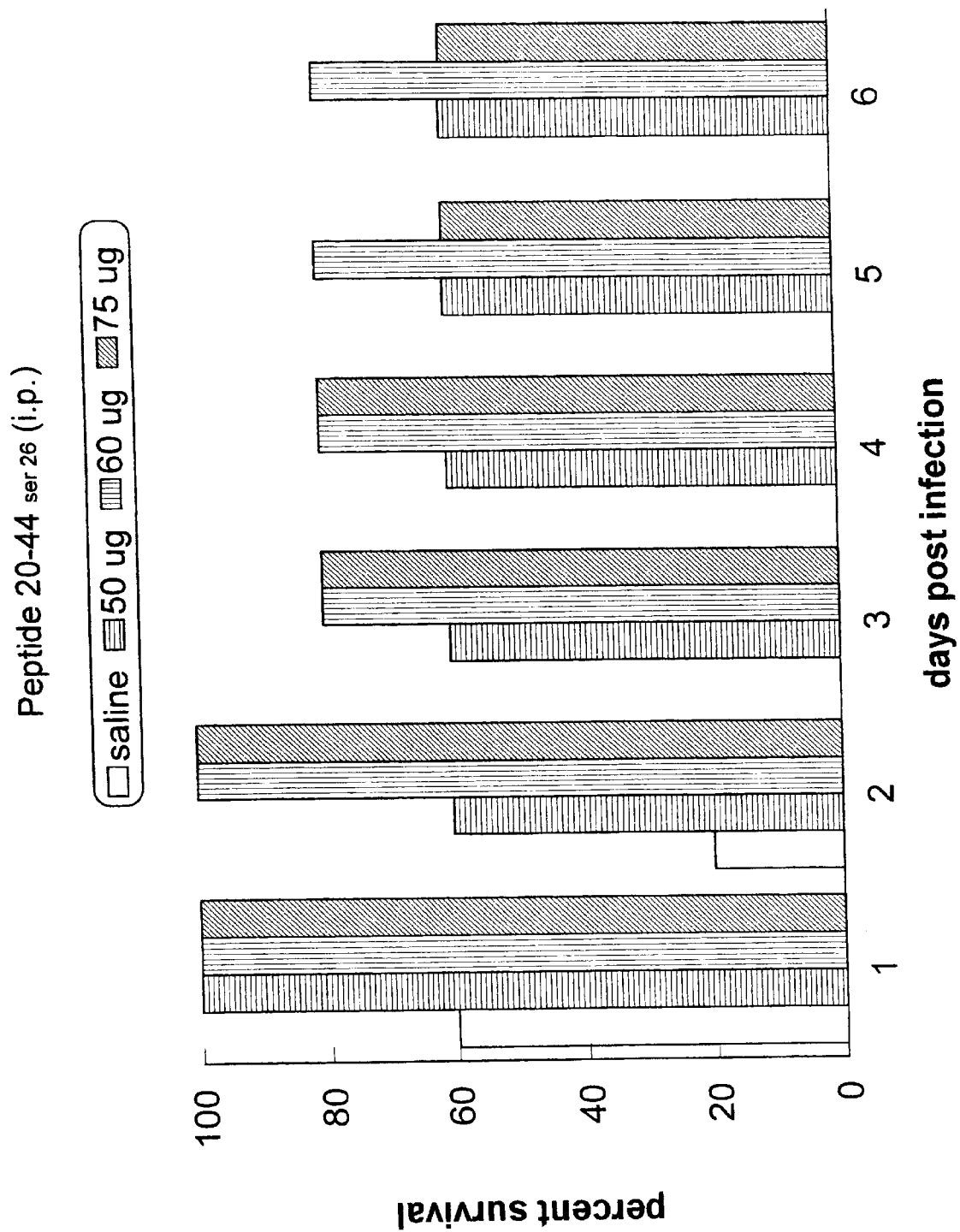
FIG. 16 is a graph showing the effects of various concentrations of peptide 20–44$_{ser26}$ administered intraperitoneally on survival of mice inoculated with live *Salmonella typhimurium* LT2.
Figure 17:
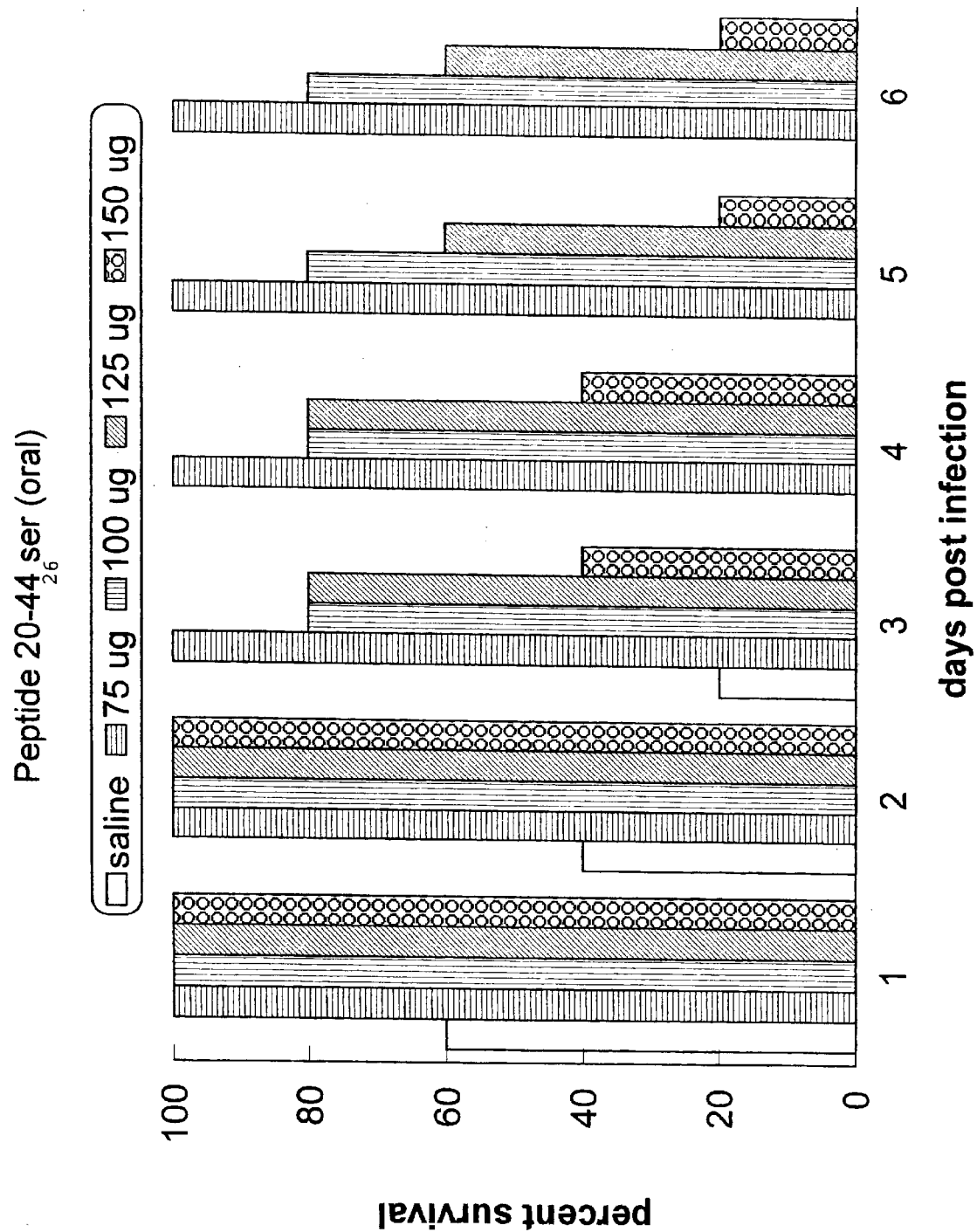
FIG. 17 is a graph showing the effects of various concentrations of peptide 20–44$_{ser26}$ administered orally on survival of mice inoculated with live *Salmonella typhimurium* LT2.

On the other hand, peptide 20–44$_{ser26}$ was highly effective at rescuing animals from lethal infection with *Salmonella typhimurium*. At day 6 post infection, doses of peptide 20–44$_{ser26}$ ranging from 25 to 100 μg saved 80 to 100% of animals (FIG. 15). The efficacy of peptide 20–44$_{ser26}$ was also observed when administered via the intraperitoneal (FIG. 16) and oral routes (FIG. 17). Optimal doses of peptide given intraperitoneally rescued 80% of mice at day 6 post infection and the oral administration of 75 μg of peptide 20–44$_{ser26}$ saved 100% of animals at day 6. Untreated animals all succumbed to infection between days 2 and 3. Survival rates with peptide 20–44$_{ser26}$ appeared to be greater than survival rates obtained with the parent peptide.

Figure 18:
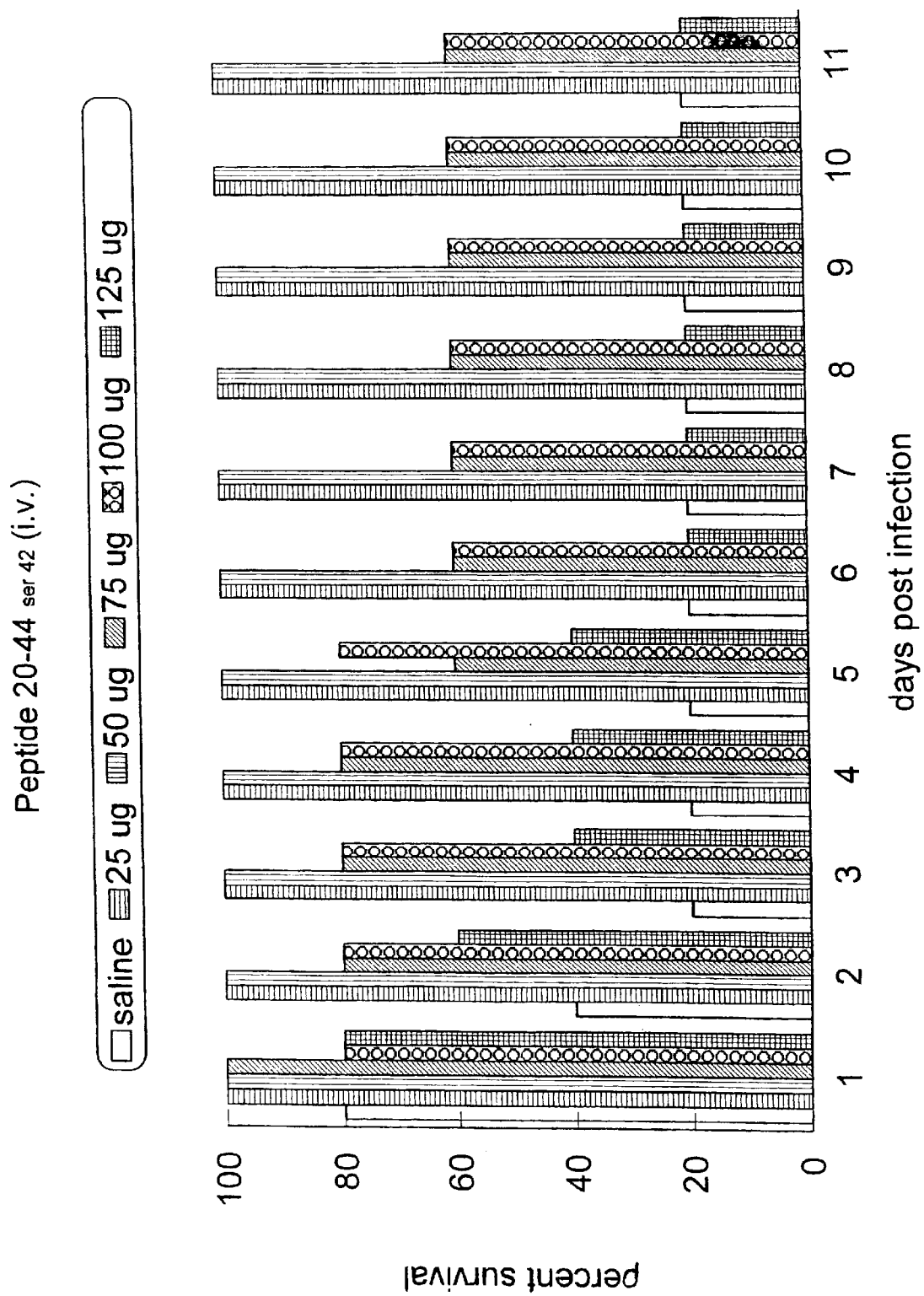
FIG. 18 is a graph showing the effects of various concentrations of peptide 20–44$_{ser42}$ administered intravenously on survival of mice inoculated with live *Salmonella typhimurium* LT2.
Figure 19:
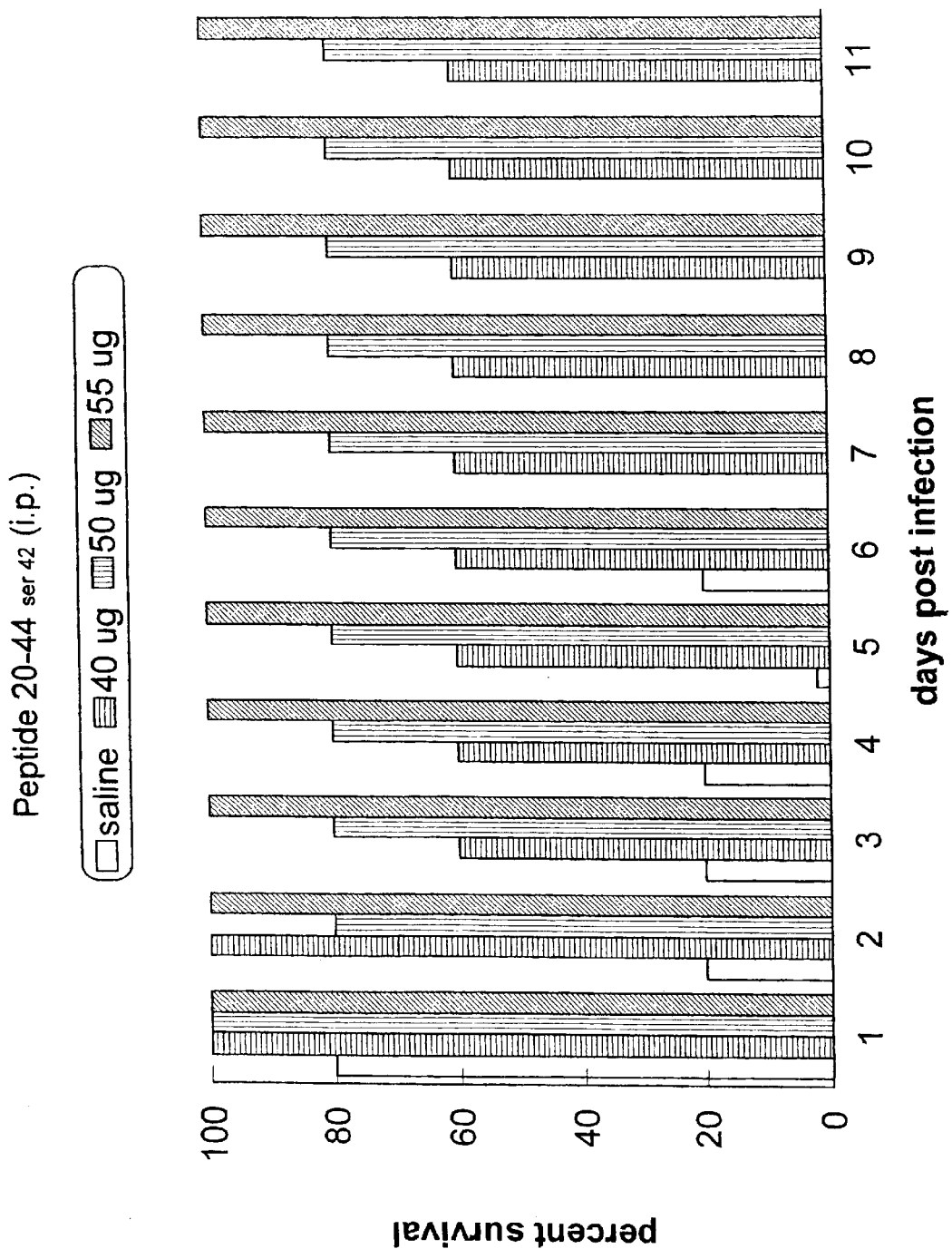
FIG. 19 is a graph showing the effects of various concentrations of peptide 20–44$_{ser42}$ administered intraperitoneally on survival of mice inoculated with live *Salmonella typhimurium*LT2.
Figure 20:
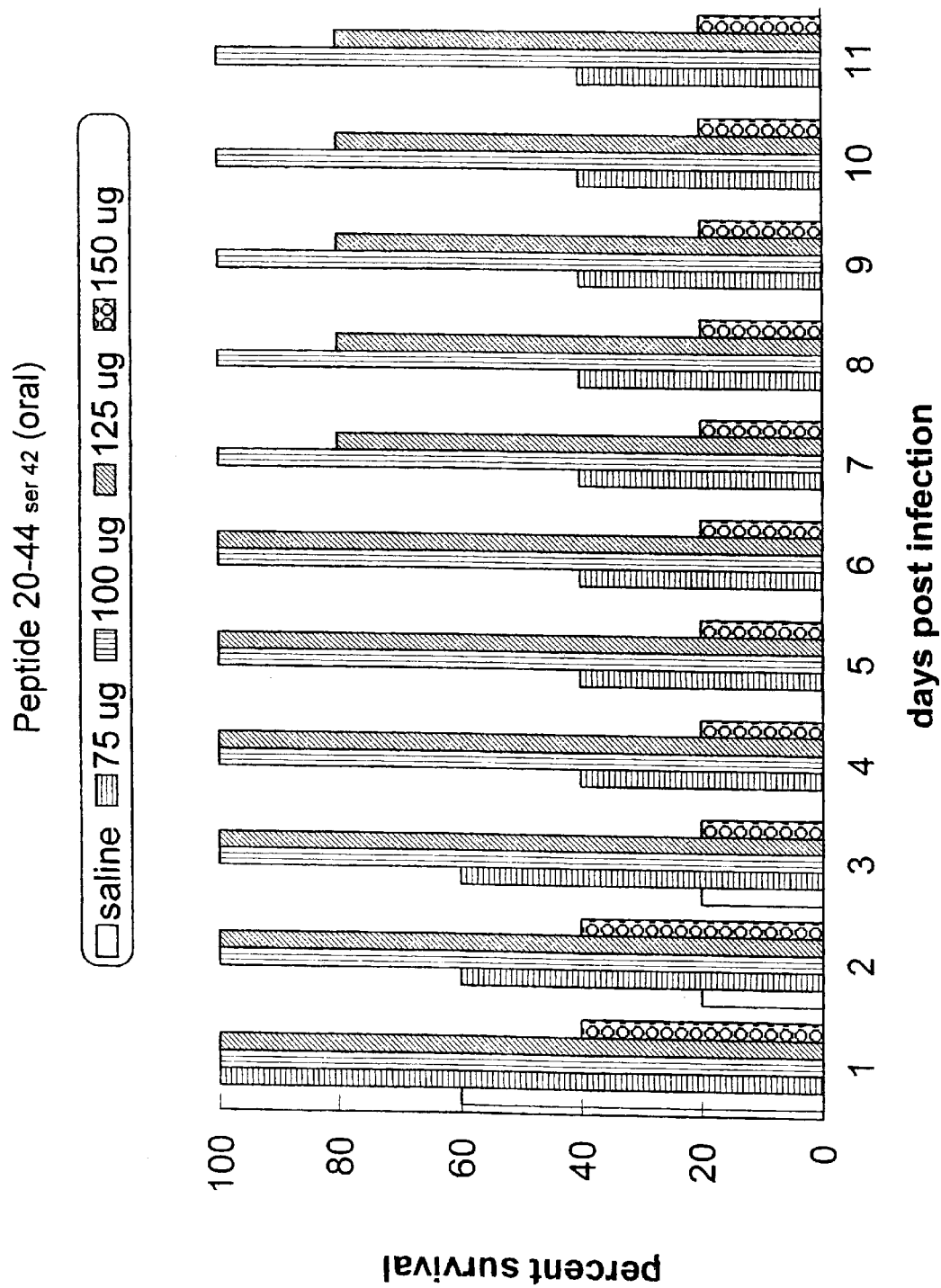
FIG. 20 is a graph showing the effects of various concentrations of peptide 20–44$_{ser42}$ administered orally on survival of mice inoculated with live *Salmonella typhimurium* LT2.

Further, peptide 20–44$_{ser42}$ appeared to be even more effective in saving animals from Salmonella infection than either the peptide 20–44 or peptide 20–44$_{ser26}$. Doses of 25 μg and 50 μg of peptide 20–44$_{SER42}$ given intravenously saved 100% of animals at 11 days post infection (FIG. 18). The three doses of peptide 20–44$_{ser42}$ given intraperitoneally (FIG. 19) saved between 60% and 100% of mice infected with Salmonella. Oral doses of peptide 20–44$_{ser42}$ between 100 and 125 μg saved 80–100% of animals from infection (FIG. 20).

In summary, these data strongly support the notion that both analogs 20–44$_{ser26}$ and 20–44$_{ser42}$ are potent antimicrobials. Another peptide (20–44$_{ACM}$) in which both cysteines were blocked with the ACM-side chain showed no activity. The two new analogs of peptide 20–44 were also active against the gram-positive bacterial pathogens, *Staphylococcus aureus* and *Enterococcus faecalis*. Further, the data described herein show that peptides 20–44$_{ser26}$ and 20–44$_{ser42}$ bind and neutralize the toxic effects of LPS endotoxin. Importantly, the in vivo data using a live infection model in mice convincingly show that the peptides 20–44$_{ser26}$ and 20–44$_{ser42}$ can rescue mice from the lethal infection caused by *Salmonella typhimurium*. The efficacy of the new peptides was demonstrated by their administration via the intravenous, intraperitoneal and oral routes.

In addition to the increased potency of peptide 20–44$_{ser42}$ and 20–44$_{ser26}$, these two peptides have technical advantages over the parent peptide 20–44. The two new analogs are easier to synthesize and purify because the internal disulfide bonding between the two cysteine residues can no longer occur. The solubility of these two new peptides is also greater than the 20–44 peptide, enabling their use at much higher concentrations than the 20–44 peptide.

The present invention further contemplates other analogs of peptide 20–44 which have antimicrobial activity. For example, instead of substituting either cysteine residue 26 or 42 with serine, they may be substituted with threonine instead.

Further, without wishing to be constrained by theory, the antibiotic activity of peptide 20–44 is probably due to a combination of charge, hydrophobicity, -helical structure, and the presence of cysteine. The presence of residues with basic groups is essential for microbicidal activity. The entire native CAP37 molecule, for example, is strongly basic. Peptide 20–44 has a charge of +2. However, at pH<6, the charge on the peptide is +4 due to the presence of two histidines.

Since a combination of charge, hydrophobicity, and -helix conformation is probably important for antimicrobial activity, the present invention contemplates that certain amino residues can be altered and/or substituted to enhance these features of the peptide. For example, the charge of the peptide can be increased by replacing residues e.g., the serine residue at position 41 with arginine, histidine and/or lysine residues as shown for example in FIG. 1, peptide analogs 20–44$_{his41}$, 20–44$_{arg41}$ and 20–44$_{lys41}$.

For example, SEQ ID NO:9, SEQ ID NO:10, and SEQ ID NO:11 are the same as SEQ ID NO:1, except the serine residue at position 41 (position 22 in SEQ ID NO:1) has been replaced with histidine, arginine, and lysine residues, respectively. SEQ ID NO:12, SEQ ID NO:13, and SEQ ID NO:14 are the same as SEQ ID NO:2, except the serine 41 residue has been replaced with histidine, arginine, and lysine, respectively. SEQ ID NO:15, SEQ ID NO:16, and SEQ ID NO:17 are like SEQ ID NO:9, SEQ ID NO:10, and SEQ ID NO:11, respectively, except the cysteine at position 26 has been replaced by a serine. SEQ ID NO:18, SEQ ID NO:19, and SEQ ID NO:20 are like SEQ ID NO:9, SEQ ID NO:10, and SEQ ID NO:11, respectively, except the cysteine at position 42 has been replaced by a serine.

SEQ ID NO:21, SEQ ID NO:22, and SEQ ID NO:23 are like SEQ ID NO:12, SEQ ID NO:13, and SEQ ID NO:14, respectively, except the cysteine at position 26 has been replaced with a serine. SEQ ID NO:24, SEQ ID NO:25, and SEQ ID NO:26 are like SEQ ID NO:12, SEQ ID NO:13, and SEQ ID NO:14, respectively, except the cysteine at position 42 has been replaced with a serine.

Replacement of amino acids (e.g. glycine) with low propensity for alpha helix formation with high propensity alanine residues would likely increase the effect of the alpha helicity, e.g., the replacement of strong helix breakers, gly 27 and gly 28 with alanine residues (see for example peptide analogs $20-44_{ala27}$, $20-44_{ala28}$ and $20-44_{ala27/28}$, of FIG. 1).

For example, SEQ ID NO:27, SEQ ID NO:28, and SEQ ID NO:29 are like SEQ ID NO:1, except that (1) the second glycine (position 27) has been replaced with alanine, (2) the third glycine (position 28) has been replaced with alanine, and (3) both the second and third glycines (positions 27 and 28) have been replaced with alanines, respectively (see FIG. 1: $20-44_{ala27}$, $20-44_{ala28}$ and $20-44_{ala27/28}$). Each of these sequences may be further modified by replacing either cysteine residue. For example, SEQ ID NO:30, SEQ ID NO:31, and SEQ ID NO:32 are like SEQ ID NO:27, SEQ ID NO:28, and SEQ ID NO:29, respectively, except the cysteine$_{26}$ has been replaced with serine. SEQ ID NO:33, SEQ ID NO:34, and SEQ ID NO:35 are like SEQ ID NO:27, SEQ ID NO:28, and SEQ ID NO:29, respectively, except the cysteine$_{42}$ has been replaced with serine.

It is further contemplated where used herein, threonine may be used as a substitute for cysteine in lieu of a serine residue (see for example peptide $20-44_{thr}$ on FIG. 1 and SEQ ID NO:36). In other words, any analog described herein in which a cysteine has been substituted with a serine, the cysteine could instead be substituted with a threonine to obtain an analog having a similar activity.

Moreover, it is further contemplated that the valine at position 36 could be substituted with a leucine, isoleucine, or alanine residue and still provide an analog which maintained antimicrobial activity as contemplated herein (see analogs $20-44_{leu36}$, $20-44_{ile36}$, and $20-44_{ala36}$ on FIG. 1 and SEQ ID NO:37, SEQ ID NO:38, and SEQ ID NO:39). Further, it is contemplated that one, two, or all three of the phenylalanine residues at positions 25, 35, and 43 could be substituted with a tyrosine residue (see analogs $20-44_{tyr25}$, $20-44_{tyr35}$ and $20-44_{tyr43}$ of FIG. 1 and SEQ ID NO:40, SEQ ID NO:41, and SEQ ID NO:42.)

It is further contemplated that alanine residues in the peptide could be replaced with valine, leucine, or isoleucine. Similarly, leucine residues could be replaced with alanine, valine, or isoleucine. Similarly, isoleucine could be replaced with alanine, valine, or leucine residues.

It is contemplated that any of the substitutions described herein for peptide 20–44 can also be made for corresponding residues of peptide 23–42.

Peptide $23-42_{ser26}$ may for example be substituted with alanine at position 27 or 28 or at both positions 27 and 28, leucine, isoleucine, or alanine at position 36, or tyrosine at positions 25, or 35, as seen in SEQ ID NO:43, SEQ ID NO:44, SEQ ID NO:45, SEQ ID NO:46, SEQ ID NO:47, SEQ ID NO:48, SEQ ID NO:49, and SEQ ID NO:50.

Peptide $23-42_{ser42}$ may be substituted with alanine at position 27 or 28 or at both positions 27 and 28, leucine, isoleucine or alanine at position 36, or tyrosine at positions 25, or 35, as seen in SEQ ID NO:51, SEQ ID NO:52, SEQ ID NO:53, SEQ ID NO:54, SEQ ID NO:55, SEQ ID NO:56, SEQ ID NO:57, and SEQ ID NO:58. Each of SEQ ID NO:4, SEQ ID NO:6, SEQ ID NO:21, SEQ ID NO:22, SEQ ID NO:23, SEQ ID NO:24, SEQ ID NO:25, SEQ ID NO:26, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, and SEQ ID NO:58, may instead have a threonine residue used in lieu of the serine residue at positions 26 or 42.

Utility

The present invention contemplates using the novel peptides described herein and/or effective subunits thereof both to treat ongoing endotoxic (septic) shock or bacterial infection and to prophylactically treat an individual who may have a risk of septic shock prior to a surgical procedure such as bowel or bladder surgery or surgical manipulation of other organs where gram-negative bacteria normally reside and could enter the bloodstream.

The peptide, synthetically or recombinantly produced, may be used as a pharmaceutical composition when combined with a pharmaceutically acceptable carrier. Such a composition may contain, in addition to the peptide and carrier, diluents, fillers, salts, buffers, stabilizers, solubilizers, and other materials well known in the art. Suitable carriers, vehicles and other components of the formulation are described, for example, in *Remingtons' Pharmaceutical Sciences,* (Mack Publishing Co., 1980). The term "pharmaceutically acceptable" means a non-toxic material that does not interfere with the effectiveness of the biological activity of the active ingredient(s). The characteristics of the carrier will depend on the route of administration.

The pharmaceutical composition of the invention may be in the form of a liposome in which isolated peptide is combined, in addition to other pharmaceutically acceptable carriers, with amphipathic agents such as lipids which exist in aggregated form as micelles, insoluble monolayers, liquid crystals, or lamellar layers which in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

As used herein, the term "therapeutically effective amount" means the total amount of each active component of the pharmaceutical composition or method that is sufficient to show a meaningful patient benefit, i.e., reduction of infection or sepsis. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of the peptide composition is administered to a mammal having a bacterial disease state. Peptide may be administered in accordance with the method of the invention either alone or in combination with other therapies.

Administration of peptide used in the pharmaceutical composition or to practice the method of the present invention can be carried out in a variety of conventional ways, such as oral ingestion, inhalation, or cutaneous, subcutaneous, intraperitoneal, or intravenous injection.

When a therapeutically effective amount of peptide is administered orally, the peptide will be in the form of a tablet, capsule, powder, solution or elixir. When administered in tablet form, the pharmaceutical composition of the invention may additionally contain a solid carrier such as a gelatin or an adjuvant. The tablet, capsule, and powder preferably contains from about 5 to 95% peptide. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, 35 propylene glycol or polyethylene glycol. When administered in liquid form, the pharmaceutical composition preferably contains from about 0.5 to 90% by weight of peptide.

When a therapeutically effective amount of peptide is administered by intravenous, cutaneous or subcutaneous injection, peptide will be in the form of a pyrogen-free, parenterally acceptable aqueous solution. The preparation of such parenterally acceptable peptide solutions, having due regard to pH, isotonicity, stability, and the like, is within the skill in the art. A preferred pharmaceutical composition for intravenous, cutaneous, or subcutaneous injection should contain, in addition to peptide an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additive known to those of skill in the art.

The invention further includes a method of treating a wound by topical application of a composition containing one or more peptides as defined herein which possess antibacterial activity in a pharmacologically effective amount to promote wound healing and/or treat infection. Other additions to the medication may be desirable such as the inclusion of epidermal growth factor also present in a pharmacologically effective amount to promote wound healing. The topical medication may take any number of standard forms such as pastes, gels, creams, and ointments.

The amount of peptide in the pharmaceutical composition of the present invention will depend upon the nature and severity of the condition being treated, and on the nature of prior treatments which the patient has undergone. Ultimately, the attending physician will decide the amount of peptide with which to treat each individual patient. Initially, the attending physician will preferably administer low doses of peptide and observe the patient's response. Larger doses of peptide may be administered until the optimal therapeutic effect is obtained for the patient, and at that point the dosage is not increased further. Without wishing to be held to a specific dosage, it is contemplated that the various pharmaceutical compositions used to practice the method of the present invention should contain about 0.1 $\mu$g to about 100 mg of peptide per kg body weight.

The duration of intravenous therapy using the pharmaceutical composition of the present invention will vary, depending on the severity of the disease being treated and the condition and potential idiosyncratic response of each individual patient. It is contemplated that the duration of each application of the peptide will be in the range of 1 to 12 to 24 hours of continuous intravenous administration. Ultimately the attending physician will decide on the appropriate duration of intravenous therapy using the pharmaceutical composition of the present invention.

Other antibiotics, intravenous fluids, cardiovascular and respiratory support could also be provided if requested by the attending physician in a manner known to one of ordinary skill in the art.

Endotoxin contamination of research reagents including aqueous buffers, cell culture media, pharmacological agents, solutions containing bioactive proteins and mediators are a common problem often leading to serious artifacts thereby confounding many experimental outcomes.

The peptide derivatives based on the CAP37 sequence 20–44 as described herein afford a convenient and efficient method for detoxifying or removing contaminating endotoxin from an aqueous sample using affinity chromatography techniques. The peptide is coupled to an inert support and a chromatographic column is prepared. Because of the strong affinity of CAP37 peptides for endotoxin, any endotoxin present in a sample applied to the column, will bind to the peptide on the support. The sample that is eluted or passes through the column will therefore be devoid of endotoxin.

Affinity chromatography is a widely used procedure for the purification of proteins (11). In general the procedure consists of coupling the peptide to a suitable matrix, such as agarose or cellulose. The matrix material is chosen such that it is hydrophilic, since this reduces non-specific interactions. It must also have large pores, and be rigid so as to be able to resist packing and washing with various buffers. It must also be chemically inert and stable to enable as wide a spectrum of solvents to be applied during the separation (11).

The coupling of peptide to matrix is according to standard procedures well known to those of ordinary skill in the art and can involve the use of a number of linking groups including cyanogen bromide, tresyl, epoxy and triazine. Coupling is performed under controlled conditions of pH, ionic strength and ion content at room temperature or 4° C. for 4–16 hours. Excess ligand is removed and the unreacted sites on the matrix are blocked to diminish non-specific interaction. The ligand-coupled matrix can be used to separate endotoxin contaminated samples either through batch absorption or by using it packed in a column. For either format the appropriate buffers need to be used. The best buffer conditions utilize either phosphate or Tris buffers (0.1–0.2 M) containing salts (NaCl, 0.1–0.5M). For the column format, the matrix-ligand slurry is loaded into a column of suitable dimensions to accommodate the sample volume. The gel is allowed to settle and the sample is loaded. The elution is performed using the buffer conditions listed, and the sample minus endotoxin that passes through the column collected in sterile -pyrogen-free containers.

Therefore, the invention as contemplated herein further comprises an affinity chromatography column or support matrix comprising a peptide as described herein.

All references cited herein are hereby incorporated by reference herein.

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims.

References

1. Shafer, W. M., L. E. Martin and J. K. Spitznagel 1984 Cationic antimicrobial proteins isolated from human neutrophil granulocytes in the presence of diisopropyl fluorophosphate. *Infect. Immun.* 45:29–35.
2. Pereira, H. A., W. M. Shafer, J. Pohl, L. E. Martin, and J. K. Spitznagel. 1990. CAP37, a human neutrophil-derived chemotactic factor with monocyte specific activity. *J. Clin. Invest.* 85: 1468–1476
3. Pohl, J., H. A. Pereira, N. M. Martin, and J. K. Spitznagel 1990. Amino acid sequence of CAP37, a human neutrophil granule-derived antibacterial and monocyte-specific chemotactic glycoprotein structurally similar to neutrophil elastase. *FEBS Lett.* 272: 200–204.
4. Morgan, J. G., T. Sukiennicki, H. A. Pereira, J. K. Spitznagel, M. E. Guerra, and J. W. Larrick. 1991. Cloning of cDNA for the serine protease homolog CAP37/ azurocidin, a microbicidal and chemotactic protein from human granulocytes. *J. Immunol.* 147: 3210–3214.
5. Brackett, D. J., M. R. Lerner, M. A. Lacquement, R. He, and H. A. Pereira. 1997. A synthetic lipopolysaccharide-binding peptide based on the neutrophil-derived protein CAP37 prevents endotoxin-induced responses in conscious rats. Infect. Immun. 65: 2803–2811
6. Pereira, H. A., I. Erdem, J. Pohl, and J. K. Spitznagel. 1993. Synthetic bactericidal peptide based on CAP37: A 37 kDa human neutrophil granule-associated cationic antimicrobial protein chemotactic for monocytes. *Proc. Natl. Acad. Sci. (USA).* 90:4733–4737
7. Fink, J., A. Boman, H. G. Boman, and R. B. Merrifield. 1989. Design, synthesis and antibacterial activity of cecropin-like model peptides. *Int. J. Peptide Protein Res.* 33: 412–421.
8. Andreu, D., R. B. Merrifield, H. Steiner, and H. G. Boman. 1985 N-terminal analogues of cecropin A: synthesis, antibacterial activity, and conformational properties. *Biochemistry* 24: 1683–1688.
9. Raj, P. A., M. Edgerton, and M. J. Levine. 1990. Salivary histatin 5. Dependence of sequence, chain length, and helical conformation for candidacidal activity. *J. Biol. Chem.* 265: 3898–3905
10. Berkowitz, B. A., C. L. Bevins, and M. A. Zasloff. 1990. Magainins: a new family of membrane active host defense peptides. Biochem. Pharmacol. 39: 65–629.
11. Ostrove, S. Affinity Chromatography: General Methods. In, Methods in Enzymology, 182: 357–375. Ed. M. P. Deutscher, Academic Press, San Diego 1990.

What is claimed is:

1. A DNA molecule comprising a nucleotide sequence encoding a peptide having the amino acid sequence:

$$R-H-X_1-X_2-X_3-X_4-X_5-X_6-X_7-H-X8-R-X_9-X_{10}-M-X_{11}-X_2-X_{13}-X_{14}-X_{15}$$

wherein:

$X_1$ is phe or tyr;
$X_2$ is cys, ser, or thr;
$X_3$ is gly or ala;
$X_4$ is gly or ala;
$X_5$–$X_8$, $X_{10}$, $X_{12}$ and $X_{13}$ are ala, leu, ile or val;
$X_9$ is phe or tyr;
$X_{11}$ is ser or thr;
$X_{14}$ is ser, thr, his, arg or lys;
$X_{15}$ is ser, cys or thr;
R is arg;
H is his; and
M is met; and with the proviso that when $X_2$ is cys, $X_{15}$ is ser or thr and when $X_{15}$ is cys, $X_2$ is ser or thr.

* * * * *

UNITED STATES PATENT AND TRADEMARK OFFICE
CERTIFICATE OF CORRECTION

PATENT NO. : 6,514,701 B1
DATED : February 4, 2003
INVENTOR(S) : H. Anne Pereira It is certified that error appears in the above-identified patent and that said Letters Patent is hereby corrected as shown below:

Column 1,
Line 28, delete the word, "it."

Columns 17 and 18,
Sequence 9, delete the following:
"Arg His Phe Ser Gly Gly Ala Leu Ile His Ala Arg Phe Val Met Thr
  1             5                    10                   15
Ala Ala Ser Ser
20"

and substitute therefore the following:
-- Asn Gln Gly Arg His Phe Cys Gly Gly Ala Leu Ile His Ala Arg Phe
   1             5                    10                   15
Val Met Thr Ala Ala His Cys Phe Gln
            20                25 --

Column 37,
Lines 28 and 29, delete the following:
"R-H -$X_1$-$X_2$-$X_3$-$X_4$-$X_5$-$X_6$-$X_7$-H-$X_8$-R -$X_9$-$X_{10}$-M -$X_{11}$-$X_2$-$X_{13}$-$X_{14}$-$X_{15}$"

and substitue therefore the following:
-- R-H-$X_1$-$X_2$-$X_3$-$X_4$-$X_5$-$X_6$-$X_7$-H-$X_8$-R-$X_9$-$X_{10}$-M-$X_{11}$-$X_{12}$-$X_{13}$-$X_{14}$-$X_{15}$ --

Signed and Sealed this

Fourteenth Day of December, 2004

JON W. DUDAS
*Director of the United States Patent and Trademark Office*